(12) United States Patent
Strand et al.

(10) Patent No.: US 7,846,382 B2
(45) Date of Patent: Dec. 7, 2010

(54) METHOD AND DEVICE FOR ULTRASONICALLY MANIPULATING PARTICLES WITHIN A FLUID

(75) Inventors: David Strand, Sherborn, MA (US); David Barrow, Cardiff (GB); Joseph Cefai, Swansea (GB)

(73) Assignee: Protasis Corporation, Marlborough, MA (US)

( * ) Notice: Subject to any disclaimer, the term of this patent is extended or adjusted under 35 U.S.C. 154(b) by 1419 days.

(21) Appl. No.: 10/516,599

(22) PCT Filed: Jun. 3, 2003

(86) PCT No.: PCT/US03/17274

§ 371 (c)(1),
(2), (4) Date: Jun. 24, 2005

(87) PCT Pub. No.: WO03/102737

PCT Pub. Date: Dec. 11, 2003

(65) Prior Publication Data
US 2006/0037915 A1    Feb. 23, 2006

Related U.S. Application Data

(60) Provisional application No. 60/394,378, filed on Jul. 8, 2002, provisional application No. 60/385,534, filed on Jun. 4, 2002.

(51) Int. Cl.
*C02F 1/32* (2006.01)
(52) U.S. Cl. .............. 422/20; 210/748.01; 210/748.02
(58) Field of Classification Search .............. 210/748, 210/151; 96/389; 95/21; 431/10; 126/93; 261/178.2
See application file for complete search history.

(56) References Cited

U.S. PATENT DOCUMENTS

| 4,055,491 A | 10/1977 | Porath-Furedi | 210/19 |
| 4,280,823 A | 7/1981 | Szonntagh | 55/15 |
| 4,523,632 A | 6/1985 | Nobukawa et al. | 165/47 |

(Continued)

FOREIGN PATENT DOCUMENTS

EP    0 773 055    5/1997

(Continued)

OTHER PUBLICATIONS

U.S. Published Patent Application 2002-0155033 to Strand et al., Oct. 24, 2002.

(Continued)

*Primary Examiner*—Duane Smith
*Assistant Examiner*—Cameron J Allen
(74) *Attorney, Agent, or Firm*—Banner & Witcoff, Ltd.

(57) ABSTRACT

Fluid-handling methods and devices for ultrasonic manipulation of fluid-borne particles comprise a fluid-handling manifold and an ultrasonic particle manipulator defining an ultrasonic cavity within the manifold. Fluid-borne particles introduced into the manifold are manipulated by controlling ultrasonic standing waves at the ultrasonic cavity. Cavities having non-uniform configurations, asymmetric standing waves and/or multiple ultrasonic cavities within the manifold are operative to control the movement of the fluid-borne particles, optionally including collecting and holding such particles, transferring particles through an intersection from one channel to another, etc. Solid phase extraction (SPE) particles, biological particles and other fluid-borne particles can be manipulated within the fluid-handling manifold.

29 Claims, 14 Drawing Sheets

U.S. PATENT DOCUMENTS

| | | | | |
|---|---|---|---|---|
| 4,523,682 | A * | 6/1985 | Barmatz et al. | 209/638 |
| 4,673,512 | A | 6/1987 | Schram | 210/748 |
| 4,877,516 | A | 10/1989 | Schram | 209/155 |
| 4,879,011 | A | 11/1989 | Schram | 204/157.42 |
| 5,164,094 | A | 11/1992 | Stuckart | 210/708 |
| 5,225,089 | A | 7/1993 | Benes et al. | 17/6 |
| 5,527,460 | A | 6/1996 | Trampler et al. | 210/198.1 |
| 5,626,767 | A | 5/1997 | Trampler et al. | 210/748 |
| 5,759,432 | A | 6/1998 | Kumar et al. | 35/495 |
| 5,831,166 | A | 11/1998 | Kozuka et al. | 73/570 |
| 6,216,538 | B1 * | 4/2001 | Yasuda et al. | 73/570.5 |
| 6,245,207 | B1 | 6/2001 | Yasuda et al. | 204/600 |
| 6,273,262 | B1 | 8/2001 | Yasuda et al. | 209/1 |
| 6,332,541 | B1 | 12/2001 | Coakley et al. | 209/18 |

FOREIGN PATENT DOCUMENTS

| | | | |
|---|---|---|---|
| GB | 2 098 498 | | 11/1982 |
| GB | 2339703 | * | 9/2000 |
| WO | WO 90/05008 | | 5/1990 |
| WO | WO 00/04978 | | 2/2000 |
| WO | WO 02/072234 | | 9/2002 |
| WO | WO02072234 | * | 9/2002 |
| WO | WO03027027 | * | 4/2003 |

OTHER PUBLICATIONS

U.S. Published Patent Application 2002-0176804 to Strand et al., Nov. 28, 2002.
U.S. Published Patent Application 2002-0199094 to Strand et al., Dec. 26, 2002.
E. Skudrzyk "Die Grundlagen der Akustic" Springer Verlag, Wien, 1954, S. 202-205, S. 807-825.
K. Asai and N. Sasaki "Ultrasonic Treatment of Slurry", Proceedings of the $3^{rd}$ International Congress on Coal Preparation, Institut National de l'Industrie Charbonniere, Brussels-Liege, 1958.
PCT International Search Report for PCT/US03/17274.

* cited by examiner

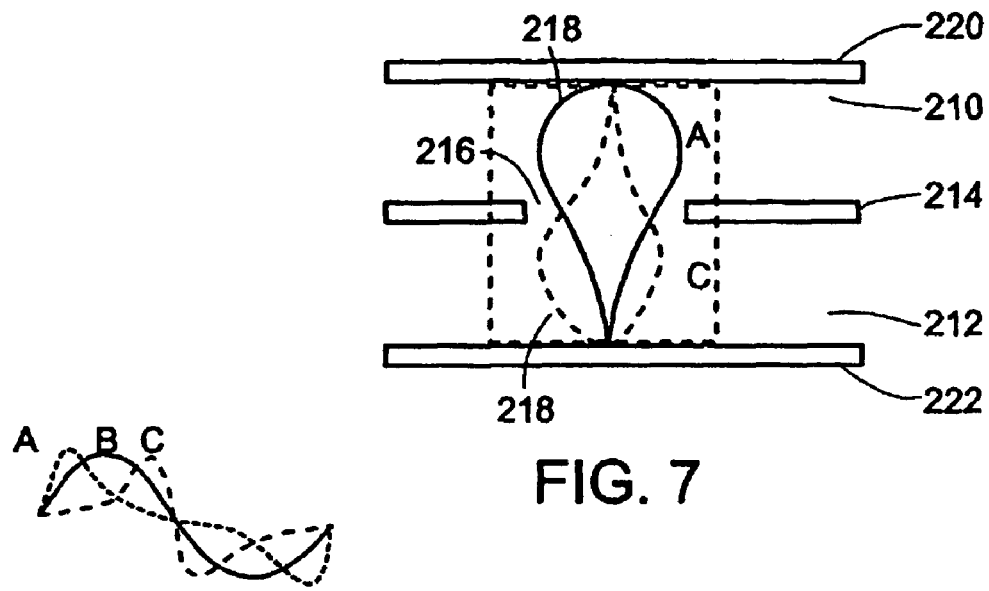
FIG. 7
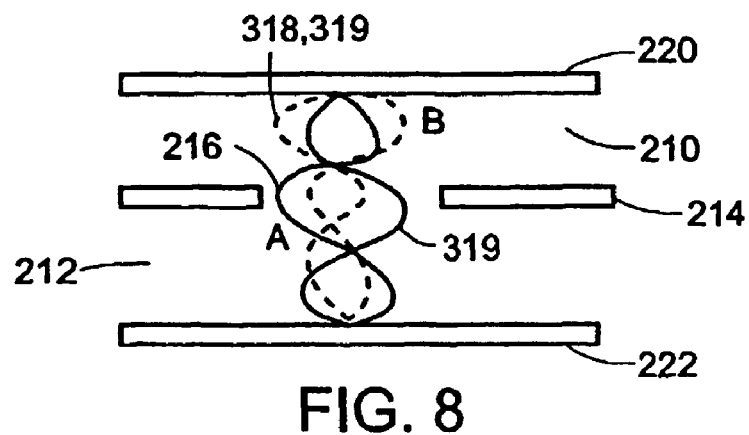
FIG. 8
FIG. 7A
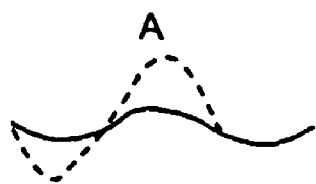
FIG. 8A
FIG. 8B
FIG. 8C

METHOD AND DEVICE FOR ULTRASONICALLY MANIPULATING PARTICLES WITHIN A FLUID

CROSS-REFERENCE TO RELATED APPLICATIONS

This application is a 35 U.S.C. §371 national Phase filing of PCT Application No. PCT/US03/17274 filed 3 Jun. 2003, which application claimed priority of the following commonly owned U.S. Provisional Patent Applications: U.S. Ser. No. 60/385,534, filed 4 Jun. 2002 and U.S. Ser. No. 60/394,378, filed 8 Jul. 2002. The PCT application designated the United States and was published in the English language on 11 Dec. 2003 as WO 03/102,737.

INTRODUCTION

The present invention relates to certain novel fluid-handling devices and methods adapted for ultrasonic manipulation of fluid-borne particles, such as for manipulation of particles suspended in a fluid using an acoustic standing wave field. In particular, the invention is directed to fluid-handling devices and methods employing them, comprising an ultrasonic transducer that can be controllably actuated to generate ultrasonic standing waves to effect movement of particles in a fluid in an ultrasonic cavity in a fluid-handling manifold.

BACKGROUND

It is known to employ acoustic energy to manipulate particles suspended in a fluid, for example, to separate different types of particles from a liquid or from each other. Prior known devices and techniques, however, do not adequately meet certain industry requirements for manipulating fluid-borne particles. In particular, there is need for devices and methods having greater functionality in collecting or manipulating fluid-borne particles for testing and analysis of fluid samples, such as chemical process stream samples, environmental fluid samples, e.g., river or lake water to be tested for pollution levels, biological fluids, e.g., blood or other fluids containing cells or other biological particles, etc.

The establishment of a standing wave in a fluid is generally believed to result in the formation of velocity nodes or antinodes to which particles migrate, depending on their compressibility or density, especially their compressibility or density relative to that of the fluid in which the particles are carried or suspended. Most solid and liquid particles (liquid particles here meaning substantially discrete globules, bubbles or other bodies of liquid in a gaseous or liquid fluid having a sufficient difference of compressibility or density to permit manipulation of the particles by ultrasonic standing waves set up in the fluid) move toward the velocity antinodes. Nodes and antinodes (referred to here generically as "nodes" in some cases) are typically at right angles to the direction of propagation of the sound waves through the fluid, and the nodes are spaced from adjacent nodes by a distance equal to one half of the wavelength of the acoustic wave. The aggregating effect of ultrasonic sound within these antinodes has already been described in the literature. From E. Skudrzyk, "Die Grundlagen der Akustic," Springer Verlag, Wien, 1954, S. 202-205, S. 807-825; L. Bergmann, "Der Ultraschall und seine Anwendungen in Wissenschafi und Technik," Verlag hirzel, Zuerich, 1954: as well as K. Asai and N. Sasaki, "Treatment of slick by means of ultrasonics," Proceedings of the 3rd International Congress on Coal Preparation, Institut National de l'Industrie Charbonniere, Brussels-Liege, 1958, all of which are incorporated herein by reference in their entirety for all purposes. The frequency to be used in the applied sound is best chosen within the magnitude of the so-called characteristic frequency f0. Using this frequency range, the effect of radiation force and cumulative acoustically induced Bernoulli forces within the antinode planes can generally be maximized.

According to U.S. Pat. No. 4,055,491, ultrasonic standing waves have been used to flocculate small particles, such as blood or algae cells, within velocity antinodes of an acoustic field, so that they settle out of the carrying liquid by gravity. But the undefined placement of the ultrasonic source and therefore low efficiency of the standing wave field due to undefined resonance boundary conditions result in high energy losses due to a considerable fraction of traveling waves.

Other methods and devices for separating different types of particles, that is, the manipulation of particulate matter in a fluid medium by the use of ultrasonic wave energy, including the segregation of dissimilar particles from a mixture of particles, are described in U.S. Pat. Nos. 4,673,512 and 4,877,516 to Schram. An ultrasonic standing wave in Schram is propagated in a liquid medium, with relative motion between the liquid and the standing wave. The different types of particles in the liquid are said to be differently influenced by the acoustic energy of the standing wave and/or the Stokes or drag forces of the liquid. The different particle types are said to move at different rates with respect to the standing wave and to be thereby progressively separated by cyclically varying the acoustic energy propagation. U.S. Pat. No. 4,673,512 introduces an interference standing wave field generated by opposing transducers which are excited with the same frequency. By controlling the phase shift between the electric excitation signals of the two acoustic sources, it is said to be possible to move-particles trapped within the antinodes or nodes of the traveling interference pattern in the dispersion. Gravity forces are said in U.S. Pat. No. 4,877,516 to cause some degree of vertical separation of different particle types, i.e., each type of particle will be located at a particular height representing an equipotential plane, dependent upon the influence of gravity on that particle type. The U.S. Pat. No. 4,887,516 suggests controlled movement of local gradients of the acoustic amplitude of the standing field perpendicular to the direction of sound propagation. Thus, particles are moved within the antinodes or nodes of the field by the Bernoulli-force which is directly related to described gradients and is acting parallel to the anti-node planes. A disadvantage of this arrangement is the requirement of mechanically moving an array to produce acoustic shadows in order to achieve desired movement of local gradients of the standing wave. Stepwise movement of the antinodes of a resonant standing wave by exciting succeeding resonance modes of a resonator system is described in PCT patent application No. PCT/AT89/00098. Although resonance boundary conditions are fulfilled in some of the described embodiments, there would appear to be considerable acoustically induced dissipation due to the resonator frequencies used, which are close to an Eigen-frequency of the transducer.

Particle separation is said to occur also in the apparatus of U.S. Pat. No. 4,523,632 to Barmetz et al. Particles of different types are said to be separated to some degree as they are carried by a liquid flow along the length of a horizontal chamber in which a standing wave is established with a wavelength that is half the height of the chamber.

In U.S. Pat. No. 4,879,011 to Schram particulate material is said to be supported in a fluid medium by means of an ultrasonic standing wave while a reaction is effected or controlled involving the particulate material, for example, reaction with the fluid medium or other material contained in the medium. Schram suggests that the standing wave can be established by opposed ultrasonic transducers producing convergent beams that compensate for attenuation of the ultrasonic energy in the fluid medium, and operate in the near field. The support provided by the standing wave is said to be able to avoid settling of the particulate material in the medium and to agitate the material. Both effects are said to enhance the rate of chemical reaction and help to ensure that the particulate material is more uniformly exposed. The process is said to have application to biological reactions, such as fermentation, and to chromatography, etc.

The application of ultrasonic standing waves has also been suggested for separating particles with various acoustic qualities in U.S. Pat. No. 4,280,823 and U.S. Pat. No. 4,523,682. Specifically, these patents suggest reliance on the differential effect of acoustic forces on particles having differences in density, speed of sound or size. Thus, a device to separate particles with various acoustic qualities is described in U.S. Pat. No. 4,523,682, wherein a low resonance mode of a vessel containing a dispersion is excited by a relatively small transducer mounted at one end of the vessel, resulting in node and antinode planes perpendicular to the transducer/vessel interface. A disadvantage of such prior methods and devices, however, lies in the fact that a further non-acoustic force— such as gravity or frictional force—is necessary in order to achieve a successful separation. Furthermore, both patents rely on having permanently and consistently constant acoustic environments. The above methods generate microscopic areas of increased particle concentration (areas of antinodes and nodes), but they only truly generate a macroscopical separation, i.e., one that extends across several wave lengths, by means of a non-acoustic force, primarily gravity.

In U.S. Pat. Nos. 5,527,460 and 5,626,767 to Trampler et al., particulate material in a fluid suspension is said to be separated and recycled by means of an ultrasonic resonance wave or field generated within a multilayered composite resonator system. A transducer, the suspension and a mirror are all said to be parallel to each other. Dimensions and frequencies resonant to the whole system but not exciting Eigen-frequencies of the transducer and mirror are said to be chosen in order to minimize thermal dissipation. Specialized applications in biotechnology are described, including an acoustic filter for mammalian cell bioreactors or the selective retention of viable cells relative to non-viable cells. The systems of Trampler et al, however, are gravity dependent to the extent they use acoustically induced forces to retain and aggregate dispersed particles and use gravity to settle and recycle the aggregates.

As noted above, there is a significant need for improved devices and methods for handling fluid-borne particles, such as fluid test samples, biological fluids and other fluids comprising fluid-borne particles. It is an object of the present invention to address the need for such improved devices and methods. In particular, it is an object of at least certain preferred embodiments of the invention to provide improved devices and methods with greater functionality in collecting and manipulating fluid-borne particles for testing and analysis of fluid samples, such as chemical processing stream samples, environmental fluid samples, e.g., river or lake water to be tested for pollution levels, and biological fluids, e.g., blood or other fluids containing cells or other biological particles, etc. These and other objects and features of the methods and devices of the present invention will be better understood from the following disclosure and detailed description of certain preferred embodiments.

SUMMARY

In accordance with one aspect, a fluid-handling device for ultrasonic manipulation of fluid-borne particles comprises a fluid-handling manifold having at least one fluid inlet port to a fluid-handling void within the manifold. The fluid-handling void includes at least a fluid channel extending from the inlet port, i.e., a channel operative to receive fluid via the inlet port and to pass such fluid in the manifold, e.g., fluid pumped or otherwise fed into the port from an exterior source. There may be more than one fluid channel within the manifold and any of such channels may include one or more straight or branched passageways and/or fluid-holding chambers or the like. The fluid-handling manifold further has an ultrasonic particle manipulator defining an ultrasonic cavity in the manifold. That is, the ultrasonic particle manipulator comprises at least one ultrasonic transducer operative to establish a standing wave at one or more locations in the fluid-handling void of the manifold, e.g., in a fluid-holding chamber along the channel, to manipulate some or all of the fluid-borne particles in a fluid flow though the channel. A reflector positioned opposite the transducer and/or one or more additional transducers can be used in accordance with known techniques to achieve standing wave fields in the ultrasonic cavity. In this regard, it will be understood from the detailed description that follows of certain preferred embodiments, that the transducer(s) may in some cases be actuated at frequencies other than their resonant frequencies in order to achieve certain aspects of the particle manipulation functionality disclosed here for fluid-borne particles in the ultrasonic cavity. The transducer may be any of those known to those skilled in the art that are suitable for a particular application of the methods and apparatus disclosed here. Optionally, in certain embodiments, the transducer employs digital signal generation. The fluid channel extends from the inlet port at least to the ultrasonic cavity, either in a straight-line path or through one or more intersections, vias, etc. within the manifold. It should be understood that any two or more channels in the manifold may or may not be in fluid communication with each other within the manifold. Two intersecting fluid passageways within the manifold may be referred to herein, alternatively, either as two different channels or as branches or portions of the same channel.

With respect to the ultrasonic particle manipulator being operative to establish an ultrasonic standing wave field in particle-bearing fluid at the ultrasonic cavity in the manifold, it is a particularly advantageous feature of certain preferred methods and devices disclosed here, that ultrasonically manipulating the fluid-borne particles comprises trapping some or all of such fluid-borne particles against flow of the fluid at one or more nodes of such standing wave. Particles trapped from a first fluid can be held in the ultrasonic cavity. The trapped particles optionally can then be acted upon in any of numerous ways and/or released into the same or a different fluid flow. For example, solid phase extraction (SPE) particles active to absorb a desired analyte can be collected from a first fluid and held in the ultrasonic cavity of the fluid-handling manifold while a second fluid known or suspected of containing the analyte in it, e.g., as a pollutant or contaminant, is then passed through the manifold to contact the trapped SPE particles. The particles can then be removed from the manifold for testing in accordance with any of innumerable known techniques for the presence of the analyte. Alternatively, the analyte can be concentrated for tested by passing a third fluid through the manifold over the particles, the third fluid being operative to strip the analyte from the SPE particles. The third fluid with the concentrated analyte can then be tested, e.g., while either still in the manifold or after being removed from the manifold. Such third fluid can be removed from the manifold, for example, via an exit port (optionally being the same port as the aforesaid fluid inlet port), tested while still in the manifold, or retained in the manifold as a storage device for use at a future time.

With respect to the ultrasonic particle manipulator being operative to establish an ultrasonic standing wave field in particle-bearing fluid at the ultrasonic cavity in the manifold, it is a particularly advantageous feature of certain preferred methods and devices disclosed here, that ultrasonically manipulating the fluid-borne particles comprises causing some or all of the fluid-borne particles to move from the fluid flowing in a first fluid channel into a fluid flowing in a second fluid channel. The particles may be moved, for example through an aperture in a wall separating the two channels from each other. The aperture may be gated or not, that is, there optionally is a moveable or otherwise controllable closure gate at the aperture such that fluid communication between the channels can be established or terminated by opening or closing the gate, respectively. In certain preferred embodiments, the manifold is operative to move fluid-borne particles from one location to another in the manifold, e.g., from one channel to another, by employing an asymmetric standing wave at the gateway or interconnection of the two channels. Fluid-borne particles in the first channel are collected at a node of a sufficiently energetic standing wave, which node is entirely or to a sufficient degree positioned in the second channel, but is sufficiently in, or proximate to, the first channel to capture particles. In certain preferred embodiments, the manifold is operative to move fluid-borne particles from one location to another in the manifold by actuation of a series of transducers to establish a corresponding series of asymmetric standing waves differing incrementally from each other. Preferably, for example, all of the asymmetric standing waves are positioned substantially adjacent each other at the gateway or interconnection of two channels, and the node of each asymmetric standing wave is somewhat more positioned in the receiving channel. In certain preferred embodiments, the manifold is operative to move fluid-borne particles from one location to another in the manifold, e.g., from one channel into another, by controlling the position of one or more standing wave nodes, i.e., by effecting a desired change in the position of the node(s) at a desired point in time. Such controlled movement of nodal position is achieved in certain such embodiments by suitably controlled actuation of the transducer(s), most preferably by using an actuating signal that is not sinusoidal, where the position of the signal maxima and minima are displaced from the normal 90 and 180 degrees of the cycle, resulting in a standing wave that can be referred to here as having asymmetric wave form. Such controlled movement of nodal position is achieved in certain such embodiments by providing a series or range of actuating electrodes varying in area. Multiple ones of such electrodes optionally are on the same transducer. Alternatively, separate transducers may be employed for each, connected to the same driving signal. When the amplitude of the driving signal is sufficiently high, and in certain embodiments, electrically impedance matched to that of the larger electrode(s), all the co-actuated transducer areas will generate a standing wave. However, as the actuation signal amplitude and hence the power decrease, the power is no longer sufficient to drive the larger areas. Suitable positioning of incrementally sized areas results in the standing wave being progressively transferred to smaller actuating areas. It will be within the ability of those skilled in the art to implement such embodiments in accordance with the principles disclosed here and to employ alternative arrangements and techniques suitable to controllably move one or more standing wave nodes in the disclosed methods and devices.

With respect to the ultrasonic particle manipulator being operative to establish an ultrasonic standing wave field in particle-bearing fluid at the ultrasonic cavity in the manifold, it is a particularly advantageous feature of certain preferred methods and devices disclosed here, that ultrasonically manipulating the fluid-borne particles comprises causing fluid-borne particles to agglomerate into aggregates of multiple particles. As used here, the term agglomerate is used in a broad sense to mean that fluid-borne particles are caused to adhere to each other, to coalesce, to flocculate or otherwise to come together so as to act or respond, e.g., to react to ultrasonic manipulation, in at least some respects in the nature of a larger particle of the same material. Optionally, for example, a series of transducers is arrayed along the fluid channel in the manifold and operated at progressively increasing or decreasing frequency to progressively agglomerate fluid-borne particles in a fluid into larger and larger particle aggregates. It will be within the ability of those skilled in the art to implement such embodiments in accordance with the principles disclosed here and to employ alternative arrangements and techniques suitable to agglomerate fluid-borne particles, optionally then moving the aggregates in accordance with the above disclosure and/or trapping the aggregates against flow.

In accordance with certain preferred embodiments, the ultrasonic cavity has a non-uniform configuration. As disclosed further below, such non-uniform configuration can be employed in conjunction with controlled varying of the standing wave field generated in the ultrasonic cavity to provide advantageous functionality. In certain such embodiments, the cavity has a transverse cross-sectional configuration that is non-uniform, that is, the cavity bore size or shape increases, decreases or otherwise changes from location to location along the travel path of the fluid through the cavity. In accordance with a significant feature of such preferred embodiments, the ultrasonic particle manipulator is operative to selectively position a node of an ultrasonic standing wave field in particle-bearing fluid in the ultrasonic cavity at any of multiple positions in the ultrasonic cavity by controlling the actuation of the ultrasonic transducer. In accordance with other preferred embodiments, the ultrasonic cavity has a cross-sectional configuration that is non-uniform in a direction substantially transverse to the direction of flow in the first fluid channel. In such embodiments, for example, the ultrasonic particle manipulator can be operative to collect fluid-borne particles at a location in the first channel of the manifold and then move the collected particles laterally, i.e., perpendicular to the direction of fluid flow through the channel, e.g., to and/or through an intersection with another fluid channel in the manifold. As described above, this significant feature can be accomplished using the non-uniform configuration of the ultrasonic cavity with controlled actuation of the standing wave field to control the position of a node at which particles were trapped or collected. In addition or alternatively, the ultrasonic particle manipulator may be operative to selectively position an ultrasonic standing wave field in the intersection and/or in the second fluid channel. A surface of the ultrasonic cavity may have a wave-like configuration along the direction of fluid communication through the intersection.

In accordance with other preferred embodiments, the ultrasonic particle manipulator is operative to generate a controllably variable asymmetric standing wave in particle-bearing fluid in the manifold, such as at the intersection of two fluid channels. More particularly, the controllably variable asymmetric standing wave in such embodiments has a node that is effective to collect and hold fluid-borne particles against the flow of fluid, and that is moveable along the axis of wave propagation, i.e., in the direction from the transducer to the reflector. The node is moveable from a first location in the first fluid-handling channel through the intersection to a second location in the second channel. Controlled actuation of the transducer may be accomplished, for example, using analog or digital electronic controls operative to continuously or step-wise vary the asymmetric standing wave. As noted above, the ultrasonic particle manipulator of the fluid-handling manifold also may use digital signal generation for controllably generating a standing wave, e.g., for controllably establishing an asymmetric standing wave in particle-bearing fluid in the manifold.

In accordance with other preferred embodiments, the fluid-handling manifold has a substantially transparent view port for examination of fluid in the manifold, most preferably for examination of collected or concentrated fluid-borne particles in the aforesaid fluid channel or in another fluid channel of the manifold that is in fluid communication with the ultrasonic cavity. In certain preferred embodiments, the view port provides observation into the ultrasonic cavity. It is a significant advantage of such embodiments, that fluid-borne particles can be collected, held (e.g., trapped against fluid flow in the manifold) and viewed or exposed to radiation through the view port while still being held by an acoustic standing wave in the ultrasonic cavity. In certain preferred embodiments, the view port provides observation into the manifold at a location other than at the ultrasonic cavity, typically a location in fluid communication with the ultrasonic cavity. Particular advantage can be realized, for example, in the observation of substantially stationary particles, such as blood cells or other biological particles or other fluid-borne particles while still in the original fluid or after exposure to one or more additional fluids in the manifold. The view port preferably is substantially transparent to visible wavelengths (i.e., light visible to the human eye), UV and/or IR radiation, as required for the intended use of the manifold. A manifold having a view port as disclosed here also may be operative to facilitate manipulation of fluid-borne particles by means of radiation. That is, the fluid-borne particles in the manifold optionally may be exposed to radiation through the view port, e.g., electromagnetic radiation. In certain preferred embodiments wherein the fluid-borne particles include biological cells or the like, radiation can be introduced through the view port to cause lysis of the cells. In certain preferred embodiments wherein the fluid-borne particles include photo-responsive particles, e.g., photo-responsive catalytic particles or the like, radiation can be introduced through the view port to actuate such photo-responsive particles. In certain preferred embodiments, a view port between ultrasonic cavities in a manifold may be used to illuminate, and optionally to activate, particles between processing stations. For example, fluid-borne particles may be illuminated between two processing stations within a manifold, one or both of the processing stations comprising an ultrasonic particle manipulator operative to establish a standing wave to manipulate the particles, such as to hold the particles against a flow of the fluid, to move the particles against or independently of the fluid flow and/or to agglomerate the particles. It will be within the ability of those skilled in the art, given the benefit of this disclosure, to implement view ports in fluid-handling manifolds as disclosed above and to implement view ports in alternative arrangements and for other purposes in accordance with the principles disclosed here.

In accordance with certain preferred embodiments, fluid-handling devices disclosed here are employed with active particles, especially for example, fluid-borne catalytic particles, reactive particles or, as mentioned above, solid phase extraction (SPE) particles effective to extract a desired component from a fluid brought into contact with the SPE particles as they are held trapped against flow in the ultrasonic cavity of the manifold, such as, e.g., a pollutant in river water, etc. Fluid-borne SPE particles or other fluid-borne active particles can advantageously be collected and held in a fluidized bed at a standing wave field in the ultrasonic cavity.

It will be understood by those skilled in the art, given the benefit of this disclosure, that the particle manipulation functionalities disclosed here can be advantageously combined as needed to meet the demands of a particular application. Thus, the use of fluid-borne SPE particles can advantageously be employed with novel aspect of the fluid-handling manifold disclosed above for exposing the particles to multiple different fluids in the manifold and/or controllably directing collected particles from one location in the manifold to another, e.g., from one channel to another within the manifold. Further, certain preferred embodiments of the fluid-handling devices disclosed here are omni-directional, that is, they are fully operative in any orientation, irrespective of gravity. Such omni-directional ultrasonic particle manipulators may comprise at least one ultrasonic transducer and an acoustic reflector positioned opposite the ultrasonic transducer, the ultrasonic transducer and the acoustic reflector cooperatively defining between them an ultrasonic cavity operative in any orientation relative to gravity to separate fluid-borne particles from fluid flowed through the ultrasonic cavity by establishing an ultrasonic standing wave field. Preferably the spacing between the ultrasonic transducer and the acoustic reflector is not more than 300 microns, in accordance with the teaching of commonly owned patent application number PCT/GB99/02384 published by the World Intellectual Property Organization as publication number WO 00/04978, the entire disclosure of which is incorporated herein by reference for all purposes.

In accordance with another aspect, a method for ultrasonically manipulating fluid-borne particles in a fluid-handling manifold comprises a combination of steps including providing and using a fluid-handling apparatus as disclosed above. Fluid comprising fluid-borne particles is introduced into the fluid-handling device via the fluid inlet port and fluid-borne particles in the fluid are ultrasonically manipulated by actuating the ultrasonic transducer to establish an ultrasonic standing wave operative to effect movement of fluid-borne particles in the fluid.

Additional aspects, features and advantages of the methods and devices disclosed here will be apparent from the following more detailed description of certain preferred embodiments.

BRIEF DESCRIPTION OF THE DRAWINGS

The aspects, features, and advantages of the present invention will be more fully understood from the following description of certain preferred embodiments, wherein reference is made to the appended drawings in which:

FIG. 7, FIG. 7a, FIG. 8 and FIGS. 8a-8c are schematic illustrations of another embodiment wherein fluid-borne particles are ultrasonically manipulated by an asymmetric standing wave field generated in an ultrasonic cavity at the intersection between first and second fluid channels in a fluid-handling manifold;

Figure 1:
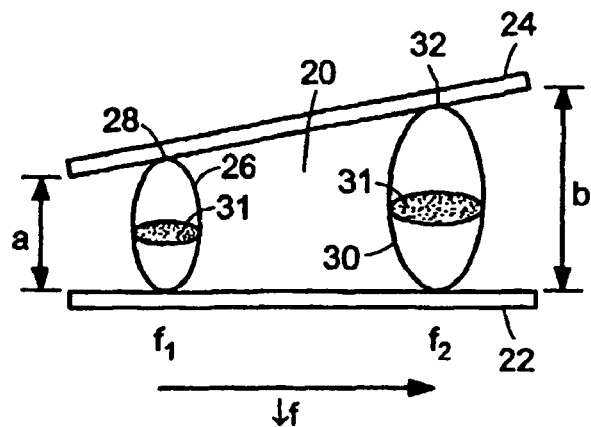
FIG. 1 is a schematic illustration of an ultrasonic cavity in accordance with one embodiment of the invention.

It should be understood that the appended drawings are not necessarily to scale. In particular, for example, wall thickness relative to other fluid channel dimensions may be exaggerated for clarity of illustration. Additionally, it should be understood that, while in certain illustrated embodiments a fluid channel is defined by wall segments up-standing from a surface of a substrate or up-standing from the plane of a laminate layer, in certain other embodiments one or more fluid channels within the fluid-handling manifold might be etched into a solid or monolithic part of a substrate, such that the channel is defined as a trough or valley. Directional references in the following discussion should generally be understood to refer to the orientation shown in the figure in question and otherwise as being consistent with the context in which the term is used.

DETAILED DESCRIPTION OF CERTAIN PREFERRED EMBODIMENTS

From the above disclosure and the following detailed description of various preferred embodiments, it will be recognized by those skilled in the art, that the novel devices and methods disclosed here have advantageous functionality applicable to manipulation of fluid-borne particles in numerous different fluid operations. Numerous embodiments of the present invention suitable for testing or analysis of a fluid are possible and will be apparent to those skilled in the art given the benefit of this disclosure, for example, methods and devices suitable as (or for use in) apparatus to perform, e.g., liquid chromatography (LC), capillary electrophoresis (CE) or other liquid-phase separation techniques, e.g., mycellular electrokinetic chromatography (MEKC or MECC), isoelectric focusing and isotachophoresis (ITP), biological fluid separations and analyses, etc. Preferred embodiments of the devices can be utilized in a wide range of automated testing and analysis of fluids. Testing or analysis of a fluid has here a broad meaning, including any detection, measurement or other characterization of fluid-borne particles or of a fluid comprising fluid-borne particles (e.g., after removal of some or all of such fluid-borne particles from the fluid). In particular, it will be recognized that the methods and devices for ultrasonic manipulation of fluid-borne particles can be used in conjunction with one or more other fluid operations, either embodied or incorporated in the same fluid-handling manifold or in other devices and apparatus connected by suitable fluid communication. In this regard, fluid-handling devices in which the present methods and devices for ultrasonic manipulation of fluid-borne particles may be advantageously incorporated are taught in commonly owned U.S. patent application Ser. No. 10/034,777 filed on 27 Dec. 2001, and U.S. patent application Ser. No. 10/034,757 filed on 27 Dec. 2001, and U.S. patent application Ser. No. 10/033,315 filed on 27 Dec. 2001, the entire disclosure of each of which is hereby incorporated by reference for all purposes. The detailed description below, for convenience, will focus on certain illustrative and exemplary embodiments.

It should be understood that reference in this description and in the claims below to "a" or "an" means, unless the context clearly requires otherwise, at least one. Thus, for example, description of a fluid-handling device for ultrasonic manipulation of fluid-borne particles as comprising a fluid handling manifold having a fluid inlet port to a fluid-handling void within the manifold should be understood to mean that the device has at least one fluid-handling manifold and that such manifold has at least one fluid inlet port and that such fluid inlet port is in fluid communication with at least one fluid handling void within such manifold.

In accordance with a first aspect, as disclosed above, a fluid-handling device for ultrasonic manipulation of fluid-borne particles comprises a fluid-handling manifold and an ultrasonic particle manipulator defining an ultrasonic cavity in the manifold. The manifold, as mentioned above, may be formed entirely or in part in a monolithic substrate, such as a unitary block of plastic, ceramic, metal or other suitable material, many of which will be readily apparent to those skilled in the art in view of this disclosure. As further described below, in certain embodiments the fluid-handling manifold is formed as a laminated structure, wherein channels, cavities and the like of the fluid-handling void can be formed by etching, micromachining, MEMs techniques or other suitable techniques which will be apparent to those skilled in the art in view of this disclosure. The manifold has at least one fluid port into a fluid-handling void comprising at least a first fluid channel which may be in the form of a cavity or passageway in the manifold, having a regular or irregular shape suitable to the needs of the particular application for which the device is intended. Fluid communication can be provided from one location to another within the manifold, e.g., from one channel to another or from one layer to another within a laminated structure, by means of through-holes or vias or by external fluid communication conduits. Additionally, various components can be mounted to the manifold, such as fluid reservoirs mounted in fluid communication to the manifold at the aforesaid first fluid inlet port or via a secondary inlet port. Additional ports can be provided in the manifold as outlet ports or additional inlet ports for introducing secondary fluids, or to provide vacuum, operative devices such as stirrers, etc. in accordance with techniques known to those skilled in the art.

The ultrasonic particle manipulator of the fluid-handling devices disclosed here comprises at least one ultrasonic transducer operative to establish an ultrasonic standing wave field in particle-bearing fluid at an ultrasonic cavity coincident with a fluid channel within the manifold. As noted above, reference in this context to a fluid channel is intended to encompass regular or irregular shaped cavities, passageways, etc. Referring now to FIG. 1, an ultrasonic cavity 20 is formed by a transducer 22 positioned generally opposite an ultrasonic reflector 24. The transducer can be actuated at any of a range of frequencies. At a first frequency represented by "f1" in FIG. 1, an acoustic or ultrasonic standing wave field 26 is established at first location 28 in the ultrasonic cavity. The ultrasonic cavity has a non-uniform configuration, specifically, the distance between the transducer and the reflector varies from one location in the ultrasonic cavity to another.

Thus, as illustrated in FIG. 1, the transducer 22, actuated at frequency "f2" (a lower frequency than f1) establishes a standing wave 30 at second location 32 in the ultrasonic cavity 20. The distance "b" between the transducer and the reflector at the second location 32 is greater than the distance "a" between the transducer and the reflector at the first location 28. Taking the downstream flow of fluid as being into the paper of FIG. 1, actuating the transducer 22 at frequency f1 is effective to collect fluid-borne particles from the fluid at a node or anti-node of standing wave 26. As used here, the term "downstream" refers to the direction of fluid flow through the fluid-handling manifold from the inlet port to the ultrasonic cavity. Changing actuation frequency f2 is effective to collect fluid-borne particles at a node of standing wave 30 at location 32 in the ultrasonic cavity. By changing the actuation frequency either continuously or step-wise from f1 to f2, collected fluid-borne particles are moved from the first location 28 in the ultrasonic cavity to the second location 32. In accordance with the aforementioned, commonly owned PCT application published as international application WO 00/04978, the spacing between a transducer and reflector defining an ultrasonic cavity in certain embodiments of the devices and methods disclosed here is not more than 300 microns. Other dimensions of the ultrasonic cavity preferably have corresponding values. With such small spacing, excellent efficacy is achieved in concentrating fluid-borne particles at lower operating voltages. Also, again referring to FIG. 1, it is generally preferred that the difference in magnitude between distance "a" and "b" is less than magnitude "a" such that the larger distance is less than twice the smaller distance. Suitable ultrasonic transducers for the fluid-handling manifolds disclosed here are commercially available, as are power sources for diving the transducers. Variable frequency oscillators (VFOs) are commercially available and can be used in the fluid-handling manifolds disclosed here to drive the ultrasonic transducer. Also, tunable ultrasonic transducers are known, including, for example, those disclosed in U.S. Pat. No. 5,759,432 to Kumar, et al and can be used in appropriate applications of the devices and methods disclosed here.

Figure 2:
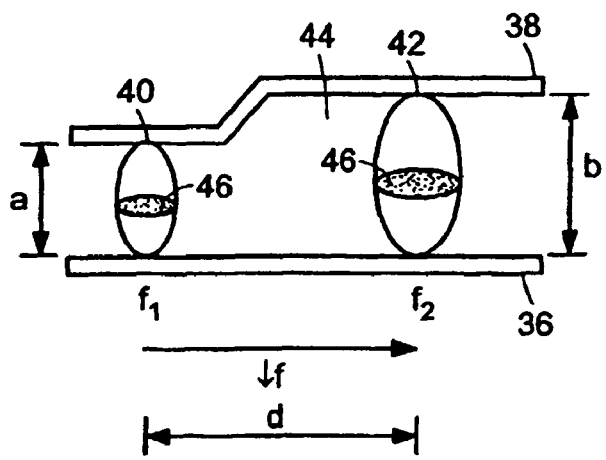
FIG. 2 is a schematic illustration of an alternative embodiment.

Referring now to FIG. 2, an ultrasonic cavity having a non-uniform configuration is formed between transducer 36 and reflector 38. The non-uniformity in this embodiment is a step-wise non-uniformity. Here, again, the flow of fluid is into the paper of FIG. 2. In accordance with such embodiments, the actuation frequency preferably would be decreased step-wise from frequency f1 to f2 to move collected fluid-borne particles from the first location to the second location. Suitable frequencies will depend in each instance on the type of particle (including the compressibility or density difference between the particle and the fluid), the energy of the standing wave, the velocity of any moving fluid, etc. In this regard, employing commercially available transducers operative within typical commercial operating ranges, first location 40 typically may be, for example, up to 30 microns distant from second location 42 in the ultrasonic cavity 44, although in certain embodiments, depending on such factors, particles may be manipulated over distances of 1 mm or even more. Collected fluid-borne particles 46 are shown at first location 40 corresponding to actuation at the higher frequency f1 and at second location 42 corresponding to lower actuation frequency f2.

Figure 3:
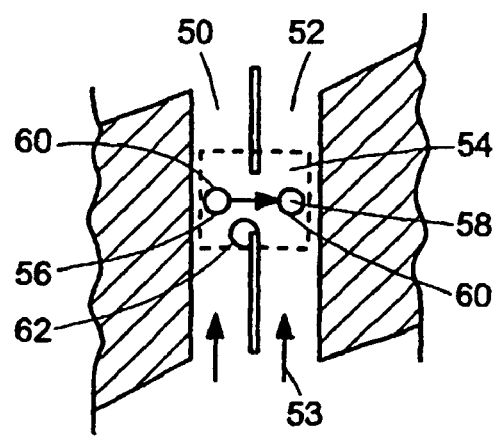
FIG. 3 is a schematic illustration of fluid-borne particles ultrasonically manipulated in accordance with one embodiment wherein first and second fluid channels are substantially parallel one another within the fluid-handling manifold, with an intersection or gateway between them for passage of fluid-borne particles.
Figure 4:
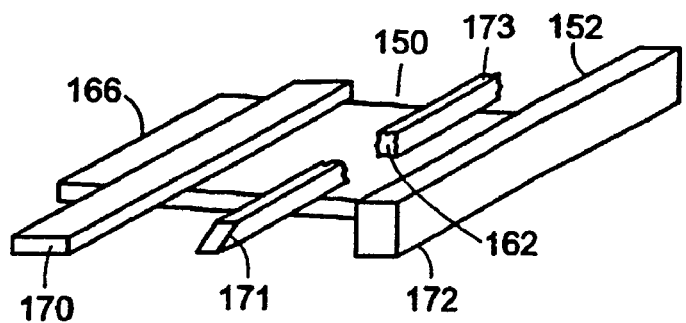
FIG. 4 is a schematic prospective illustration of channels in a fluid-handling manifold in accordance with the embodiment of FIG. 3.

FIG. 3 is a schematic overhead view of the intersection between two substantially parallel fluid channels within a fluid-handling manifold. For purposes of illustration, the direction of fluid flow in first channel 50, represented by arrow 51, is taken to be the same as the direction of fluid flow in the second channel 52, represented by arrow 53. The flow can be understood to be substantially in the plane of the paper of FIG. 3. An ultrasonic cavity 54 is defined by a transducer and reflector, one line above the plane of the paper in FIG. 3 and the other below, such that they are substantially facing each other across channels 50 and 52. Ultrasonic cavity 54 has a non-uniform configuration, such as in the embodiment of FIG. 1 or FIG. 2. Thus, the distance between the reflector and the transducer is smaller at first location 56 then at second location 58 within the ultrasonic cavity. Actuation of the transducer at a first frequency is effective to collect fluid-borne particles 60 at a standing wave node established at location 56. Reducing the actuation frequency is effective to move or reform the ultrasonic standing wave at second location 58, thereby moving collected particles 60 through intersection 62 to the second location 58. Accordingly, fluid-borne particles traveling in channel 50 are collected at first location 56 and then moved by changing the actuation frequency of the transponder through the intersection 62 into the second channel 52. The particle 60 can be held at second location 58 either permanently or temporarily, after which they can be released into the flow of channel 52 or returned to channel 50 by reversing the change in actuation frequency of the transponder. FIG. 4 is a perspective view, partially broken away, of an embodiment in accordance with FIG. 3. Channels 150 and 152 corresponding to channels 50 and 52 of FIG. 3 are seem to be formed by wall portions 170-173 in cooperation with a transponder 166 below the fluid flow channels and a corresponding ultrasonic reflector (not shown) above the channels. Thus, an ultrasonic cavity is formed in a location of intersection 162 between the two channels. Wall component 172 is seem to be substantially higher than component 170, with components 171 and 173 being an intermediate height, such that the ultrasonic cavity has a non-uniform configuration and is operative in the manner described in connection with FIGS. 1-3. It can be seen, therefore, that the ultrasonic transducer is operative to establish ultrasonic standing wave fields having an axial direction of standing wave propagation substantially perpendicular to the direction of fluid flow through the intersection. It will be recognized that in an embodiment according to FIG. 3 or FIG. 4, the ultrasonic particle manipulator can be designed so as to be operative to establish a standing wave field in the intersection between first and second channels.

In accordance with preferred embodiments, acoustically transparent materials are used in the area of the gate or intersection between channels to produce less interference or disruption of the intended standing wave pattern. Suitable acoustically transparent materials include, for example, polyethylene and other polyolefins, since these materials are relatively inexpensive, sufficiently chemically and thermally stable for many intended use environments, and can be formed or machined in accordance with known techniques. It is advantageous if the acoustically transparent walls have a wall thickness of half or an integral multiple of half a wavelength in the wall material at applied frequency fn. When plexiglass is used as wall material, a wall thickness of 2.7 mm ensues at fn=2 MHz for 4.lambda./2.

In certain preferred embodiments mentioned above, wherein the gap between the transducer and the reflector is not more than about 300 microns and other dimensions of the ultrasonic cavity have corresponding values, it is generally preferred that the lateral dimension of wall segments 171 and 173 in FIG. 4 (that is, the dimension in the direction of flow through the intersection, or transverse to the direction of flow in channels 150 and 152) is, e.g., about 10 microns to 30 microns. The longitudinal or axial dimension (that is, the dimension parallel to the direction of flow in channels 150 and 152) of intersection 162 can vary considerably. The opening generally should be adjacent to the standing wave field to move particles through the gap. Suitable methods are mentioned above for producing fluid-handling manifolds having flow channel configurations in accordance with these preferred embodiments.

Figure 16:
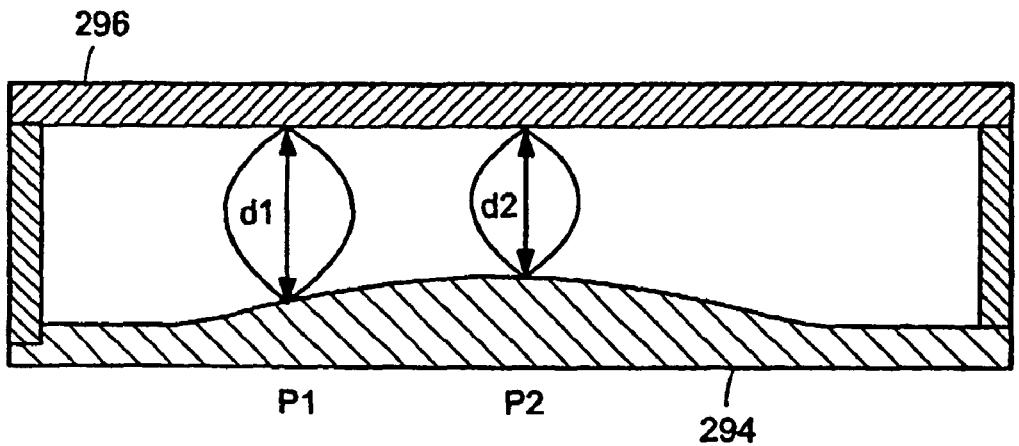

As discussed further below, the ultrasonic cavity in alternative embodiments of the fluid-handling manifold has a flow-wise non-uniform configuration, more specifically, a configuration that is non-uniform in the direction of flow (as opposed to the embodiments described above having a configuration that is non-uniform in a direction transverse to flow). Thus, in FIGS. 1 and 2, flow can now be taken as from left to right or from right to left in the plane of the paper. In such embodiments, the fluid-handling manifold is operative to collect fluid-borne particles, preferably to collect and hold such particles against the flow of fluid in the channel, at any of multiple positions (e.g., at either of two positions in an embodiment according to FIG. 2) along the longitudinal or axial dimension of the channel, or in the direction of flow, by controlled actuation of the transducer. Such embodiments are discussed further below in connection with FIG. 9. In general, the configuration of the ultrasonic cavity can either decrease or increase in the direction of flow, i.e., in the downstream direction. The non-uniformity can be a continuous change in the gap or distance between the transducer and the reflector, e.g., where one slopes relative to the other as in the embodiment of FIG. 1, or in a step-wise fashion as in the embodiment of FIG. 2. Also, as further discussed below, the distance between the reflector and transducer in the ultrasonic cavity can vary in a wavelike fashion (see FIGS. 13 and 16).

Figure 5:
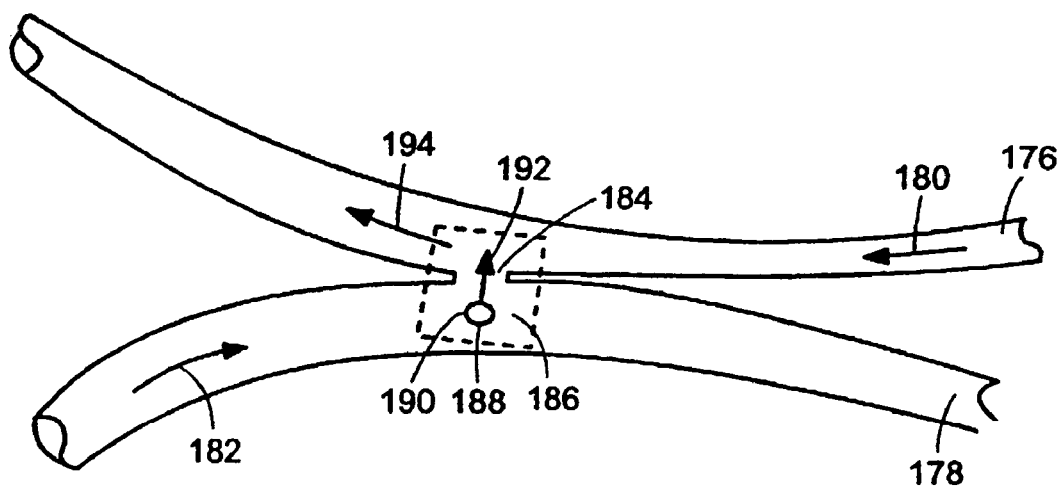
FIG. 5 is a schematic illustration of ultrasonic manipulation of particles in accordance with an alternative embodiment wherein first and second fluid channels intersect each other substantially tangentially within the fluid-handling manifold.

Referring now to FIG. 5, a schematic representation is seen of a first flow channel 176 and a second flow channel 178 for carrying fluid flows in a fluid-handling manifold in accordance with the methods and devices disclosed here. Flow channels 176 and 178 are shown having flow in opposite directions, as represented by flow arrows 180 and 182. The channels are seen to intersect each other substantially tangentially at intersection 184 located in ultrasonic cavity 186 defined by an ultrasonic transducer and reflector (not shown). Fluid-borne particles 188 collected at first location 190 in channel 178 are moved to channel 176, as indicated by arrow 192. In accordance with an optional feature of this embodiment, collected particles 188 are released into the flow of channel 176, as indicated by arrow 194.

Figure 6:
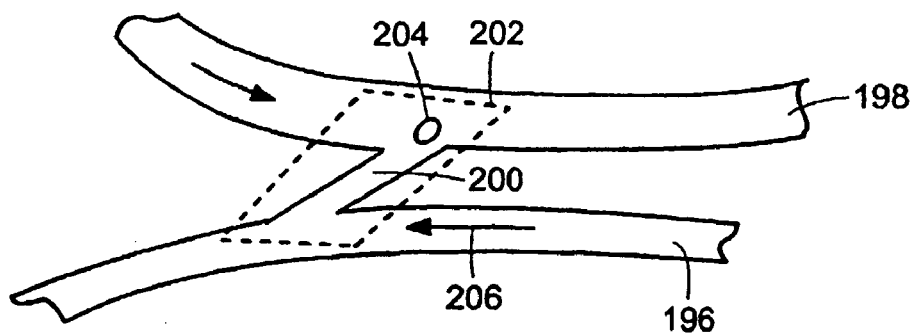
FIG. 6 is a schematic illustration of another embodiment wherein the intersection between first and second fluid channels within the fluid-handling manifold comprises an orifice.

In accordance with certain embodiments, the intersection between first and second fluid flow channels comprises a venturi orifice. Referring to FIG. 6, first flow channel 196 and second flow channel 198 are seen to have an intersection formed as an orifice 200. An ultrasonic cavity indicated by line 202 is formed by an ultrasonic particle manipulator of the manifold in accordance with the principles disclosed above, comprising an ultrasonic transducer and an acoustic reflector (not shown) overlying and underlying, respectively, the channels 196 and 198 in the area of the intersection. Controlled actuation of the transducer is effective to collect and hold fluid-borne particles from fluid flowing in channel 198. Specifically, collected particles are held at location 204 against the flow of fluid in channel 198. The collected particles can be transferred through interface 200 by the effect of fluid flowing in channel 196, as represented by arrow 206. The pressure at the inlet and outlet of the orifice is dependant in part on the respective pressures in the two adjacent, parallel channels. Thus, it will be recognized by those skilled in the art, that controlling the location of the fluid-borne particles collected at location 204 can be accomplished through balancing the effect of the fluids flowing in the two channels, together with controlled actuation and deactuation of the transducer to collect particles or release them, respectively. In view of the principles disclosed above, it will be apparent to those skilled in the art, that the orifice in the embodiment of FIG. 6 optionally can be operative in either or both directions through the intersection 200.

Referring now to FIG. 7, FIG. 7a, FIG. 8 and FIGS. 8a-8c, additional embodiments are seen of the fluid-handling devices disclosed here comprising a fluid-handling manifold wherein the fluid-handling void has at least two fluid flow channels that intersect each other. Preferably the channels are substantially parallel to each other, divided by a thin, uniform wall of acoustically transparent material. The intersection is a passageway through the dividing wall, in accordance with the principles discussed above. The ultrasonic particle manipulator of such embodiments is operative to generate a controllable variable asymmetric standing wave in particle-bearing fluid at the intersection. The asymmetric standing wave is controllably variable, such that a node of the standing wave is moveable from one channel to the other through the intersection. In certain embodiments, control of the asymmetric standing wave moves particles to and from a view port (or between different view-ports), from one processing station to another, etc. Preferably, the standing wave has a single node, as best seen in FIG. 7. The schematic illustration of FIG. 7 shows parallel channels 210 and 212, in each of which the flow can be in either direction. The channels are separated by thin, uniform, acoustically transparent dividing wall 214 that forms intersection 216 in the nature of a gap or opening in wall 214. The primary node of acoustic standing wave 218 is seen in a first condition represented by wave line "A" to be positioned in channel 210. In a second condition, represented by standing wave line "C" the node of standing wave 218 is seen to be positioned in channel 212. Accordingly, by controlling the asymmetry of a standing wave, and moving a node of an asymmetric standing wave through an intersection between channels, fluid-borne particles collected in one of the channels can be moved into the other channel. The standing wave 218 of FIG. 7 preferably is produced by an ultrasonic particle manipulator comprising a reflector 220 and a transducer 222 positioned substantially coplanar to the reflector on the opposite side of the intersection. Thus, the axial direction of wave propagation is transverse or perpendicular to flow in channels 210 and 220, and is substantially aligned with the direction of flow through the intersection. Suitable controls for actuation of the transducer include, for example, analog and/or digital electronic controls operative to continuously vary the position of the asymmetric standing wave through the intersection. Alternatively, analog electronic controls operative to step-wise vary the position of the asymmetric standing wave through the intersection can be used. Suitable analog and digital electronic controls are commercially available and will be apparent to those skilled in the art given the benefit of this disclosure. FIG. 7a illustrates the actuation wave profile corresponding to generating standing wave 218 in asymmetric condition "A" and asymmetric condition "C" discussed above, as well as intermediate condition "B." In the intermediate condition "B" standing wave 218 typically will be a symmetrical standing wave with its node centered in the intersection 216. FIG. 8 and FIGS. 8a-8c illustrate an alternative embodiment wherein the asymmetric standing wave is multi-nodal, that is, wherein the standing wave has multiple nodes, one of which is dominant. In condition "B" the dominant node 319 of standing wave 318 is located in channel 210. In intermediate condition "A," corresponding to actuation curve "A" in FIG. 8a, the dominant node 319 is located in intersection 216. It will be readily understood that under the condition of actuating wave "C" as seen in FIG. 8c, dominant node 319 would be positioned in channel 212. Suitable power sources for driving the ultrasonic transducers of the devices disclosed here are commercially available and will be apparent to those skilled in the art given the benefit of this disclosure. Preferably alternating current power sources are used for driving the ultrasonic transducers. In this regard, as noted above, the transducers may be driven at their resonant or non-resonant frequencies in order to produce suitable standing waves, including moving standing waves and asymmetric standing waves in accordance with the principles discussed above.

In accordance with certain highly preferred embodiments, the fluid-borne particles manipulated in the fluid-handling manifolds of the devices and methods disclosed here are solid phase extraction (SPE) particles. Such particles can be, for example, uniform diameter microspheres active to absorb a desired analyte from the fluid treated in the manifold. In accordance with certain preferred embodiments, the fluid-borne particles are operative to extract a desired analyte while traveling in a fluid sample in a channel in the manifold. The SPE particles can be then collected and held at a desired location employing the inventive aspects disclosed above. Once collected, the particles can be moved to a different channel for evacuation from the manifold or further processing or treatments within the manifold. For example, the SPE particles can subsequently be exposed within the manifold to a flow of a second fluid, such as a solvent for the analyte. Such solvent flow can be carried in a second channel, so as to avoid substantial contamination by the sample fluid. In alternative embodiments, SPE particles are introduced into the manifold and collected and held at a location using the standing wave technology disclosed above, after which a fluid sample is introduced and flowed passed the SPE particles. In such embodiments, the SPE particles advantageously are held at a desired location to act in the nature of a fluidized bed to extract a desired analyte from the sample fluid. Again, the SPE particles can then be subjected to a flow of a second fluid, such as a solvent for the analyte. This can occur either at the same location where the SPE particles performed the extraction as a fluidized bed, or at a different location within the manifold.

Figure 9:
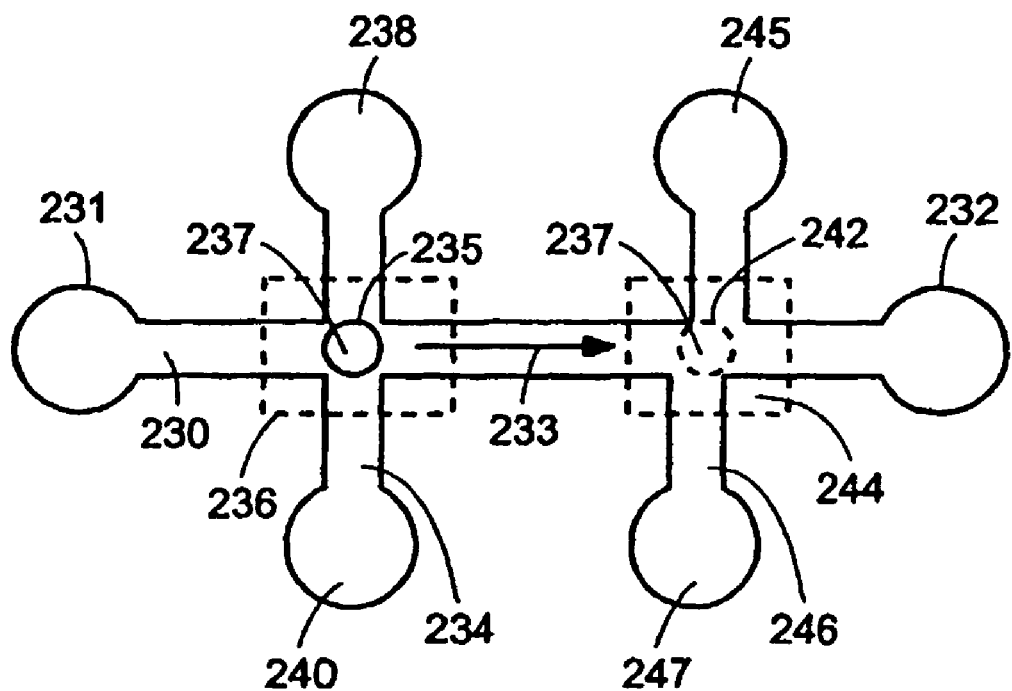
FIG. 9 is a schematic illustration of another embodiment wherein fluid-borne particles are ultrasonically manipulated from a first intersection of fluid channels to a second intersection of fluid channels within a fluid-handling manifold.

Embodiments having intersecting fluid channels, as schematically illustrated in FIG. 9, can advantageously be employed in solid phase extraction processes. Primary channel 230 extends from an inlet port 231 to an outlet port 232, such that flow through channel 230 is in direction of arrow 233. Fluid can be introduced into channel 230 via inlet port 231, for example, fluid comprising fluid-borne SPE particles. The particles can be collected at location 235 within ultrasonic cavity 236 established by an ultrasonic transducer and reflector (not shown). The SPE particles 237 held at location 235 can act as a fluidize bed to extract an analyte component of a second fluid introduced into the fluid-handling manifold at second inlet port 238. It can be seen that inlet port 238 is in fluid communication with a second fluid channel 239 which intersects with primary channel 230 at location 235. Channel 239 has an outlet port 240. Subsequent to such treatment of the secondary fluid at location 235, the SPE particles can be released to flow to location 242 at which they are collected and held by means of a standing wave of sufficient energy and configuration, generated at ultrasonic cavity 244 defined by a second transducer and second reflector (not shown). At location 242, the SPE particles can be exposed to a flow of a third fluid introduced into the fluid-handling manifold at third inlet 245. It can be seen that inlet 245 is in fluid communication with third channel 246 having outlet port 247. The SPE particles being held at location 242 will be exposed to fluid introduced at inlet port 245, since channel 246 intersects with primary channel 230 at location 242. As noted above, the third fluid could advantageously be a solvent for the analyte extracted by the SPE particles from the sample fluid passed through channel 239. In such embodiments, the solvent is collected at outlet port 247 for further processing, such as liquid chromatography for other fluid operations or analyses.

In accordance with the principle disclosed above, it will be understood that the transfer of the SPE particles from location 235 at the first intersection to location 242 at the second intersection can optionally be accomplished using an ultrasonic cavity having a non-uniform configuration and spanning both locations. Such embodiments, however, should meet the size and dimension constraints discussed above. Similarly, a single ultrasonic cavity spanning the two intersection locations could move the SPE particles from one location to the next by appropriate manipulation of the configuration of an asymmetric standing wave. The discussion of FIG. 7 and FIG. 8 is relevant here to such embodiments. Furthermore, the discussion above regarding the sequential exposure of SPE particles to different fluids at different locations is applicable also to the treatment of fluid-borne biological cells or other biological particles.

Exemplary of the methods disclosed here, and referring to the structural features of FIG. 9, biological particles can be introduced in a primary flow through inlet port 231 and collected and held at location 235 for exposure to a second fluid introduced via inlet port 238. Subsequently, the particles are moved to location 242 for exposure to a third fluid introduced at inlet 245. Particles 237, upon being released from location 242, can be collected for further analysis or disposal. Optionally, particles 237 can be collected via outlet port 232 in a flow introduced, for example, via inlet port 231. Alternatively, particles 237 can be collected via outlet port 247, for example, in a flow introduced via inlet port 245. Preferably, the standing wave is de-actuated for collection and removal of the particles from the manifold.

It will be recognized by those skilled in the art, given the benefit of this disclosure, that in certain embodiments of the methods and devices disclosed here, the fluid-borne particles need not be in a flowing medium. Rather, the particles can be held in a reservoir or other similar structures in a manifold. The particles can be systematically moved using the ultrasound field rather than fluid flow. Similarly, fluid samples comprising fluid-borne particles may be collected in a microtiter plate, with ultrasonic manipulation employed to concentrate particles in each well into a focused spot.

In accordance with certain alternative embodiments, the manifold further comprises a view port for visual observation of particles collected and held at a location in the ultrasonic cavity of the manifold. For example, blood cells or other biological particles may advantageously be viewed at location 242 or 235 in the embodiment of FIG. 9. The view port preferably comprises a fluid tight optically clear wall portion of the manifold overlying or otherwise approximate the location of the standing wave at which the fluid-borne particles will be held by a standing wave generated by the ultrasonic particle manipulator of the manifold. In alternative embodiments, the view port is provided at an otherwise convenient location and the fluid-borne particles are held in position approximate the view port by controlling fluid flow in the fluid channel.

Figure 10:
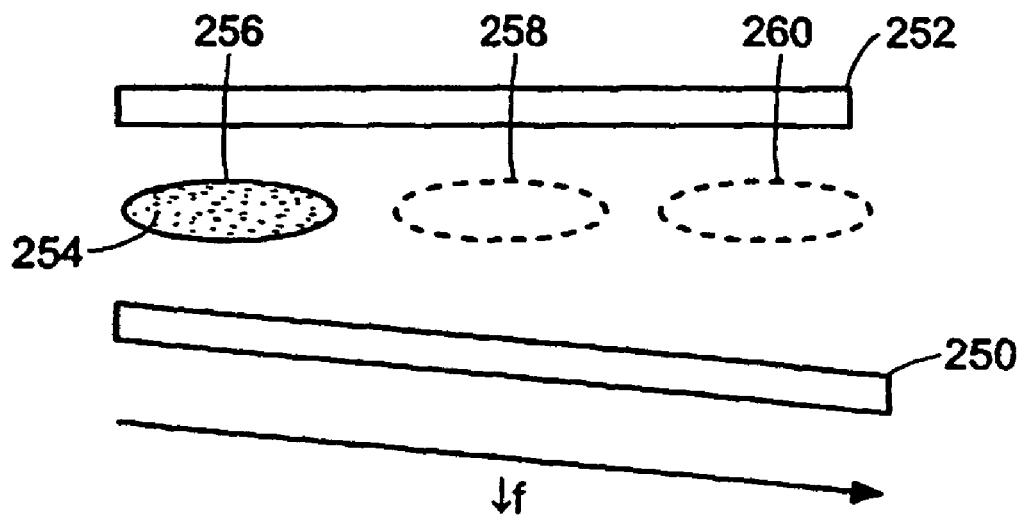
FIG. 10 is a schematic illustration of another embodiment wherein fluid-borne particles are ultrasonically manipulated in an ultrasonic cavity operative as a shear flow column.

Referring now to FIG. 10, an ultrasonic cavity is seen to have a non-uniform configuration in accordance with the principles disclosed and discussed above. Transducer 250 cooperatively with reflector 252 produces a standing wave in the ultrasonic cavity, having frequency "f." A node of the standing wave is operative to collect fluid-borne particles in a fluid passing through the ultrasonic cavity. In accordance with certain preferred embodiments, such node 254 at which fluid-borne particles 256 are collected is operative to hold the particles 256 against a flow of fluid through the ultrasonic cavity. By varying the frequency of the ultrasonic standing wave, node 254 can be moved in the ultrasonic cavity as indicated by phantom lines at locations 258 and 260. Accordingly, a shear flow column can be achieved in embodiments according to the arrangement of FIG. 10.

Figure 11:
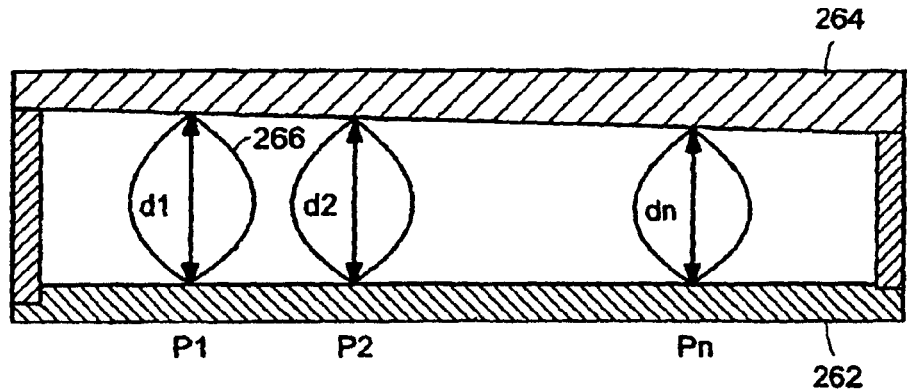
FIGS. 11-16 are schematic illustrations of ultrasonic cavities in fluid-handling manifolds in accordance with additional embodiments.

Various alternative embodiments are illustrated in FIGS. 11-16. More specifically, ultrasonic cavities having non-uniform configurations are formed by a reflector and a transducer in accordance with the principles discussed above. In FIG. 11 the ultrasonic chamber is constructed such that the chamber contacting surface of the transducer 262 is held fixed at a distance from the chamber contacting surface of the reflector 264. The distance between the transducer and the reflector is different at different points within the cavity. Specifically, the reflector provides a sloping surface relative to the transducer. At point P1 in the cavity, the standing wave field propagation path is indicated by line "d1." Similarly, at point P2 the standing wave field propagation path is "d2." Correspondingly, the standing wave field propagation path at any point Pn in the cavity can be represented as "dn." It can be seen that "d1" is greater than "d2" and "d2" is greater than "dn." The standing wave frequency f1 at location P1 is directly proportional to the distance of path "d1" since "d1" is equal to (n)×(¼ wavelength of standing wave), where "n" will vary depending on the medium in which the standing wave is operating. Without wishing to be bound by theory, the frequency typically wound not go below about 3 MHz in systems employing liquid as the fluid, because of cavitations. Without wishing to be bound by theory, it is generally understood that this is the condition that needs to be satisfied for the standing wave field to be established. Furthermore, the wavelength of the standing wave is the speed of sound in the medium present in the cavity divided by the frequency of the standing wave. Therefore at any given transducer actuation frequency, standing waves will develop at points in the cavity where the frequency and hence the wavelength of the ultrasonic wave matches or corresponds to the distance between the transducer and the reflector. If the actuation frequency of the transducer is changed, one or more standing waves will develop at different locations in the ultrasonic cavity, specifically, where the new standing wave wavelengths match the reflector-to-transducer distance.

Advantageously, a gradual change in the distance between the reflector and transducer can be achieved by properly configuring or structuring the reflector in the manifold and/or by placing the reflector at a specific desired angle to the transducer. The actuation frequency of the transducer can be tuned to establish standing waves at different, pre-determined points in the cavity. In accordance with the principles discussed above, the device can then concentrate particles at different locations in the ultrasonic cavity, depending on the frequency of actuation and/or allow particles held in one part of the chamber using one actuation frequency to be transferred to another location by changing the actuation frequency. Movement of the fluid-borne particles is controlled in this manner, within the constraints noted above regarding sufficiently small steps. The distance to be traveled by particles at each step change in actuation frequency should be small enough to ensure that the particles remain under the influence of at least one of the standing wave field positions.

Figure 12:
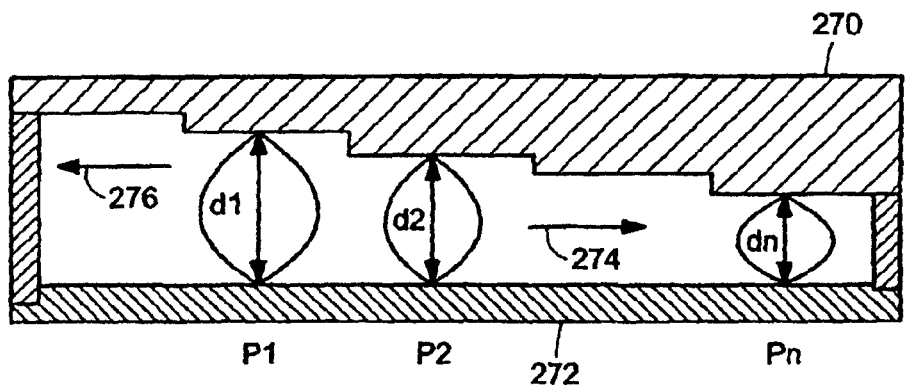

It will be readily understood from this disclosure, that the foregoing principle is particularly important under flowing conditions, that is, where the particles are being held by the standing wave against a flow of fluid through the chamber. FIG. 12 illustrates an ultrasonic cavity wherein the transducer 270 has a step-wise configuration such that the distance between the reflector and the transducer 272 decreases in the direction of flow represented by arrow 274.

Figure 13:
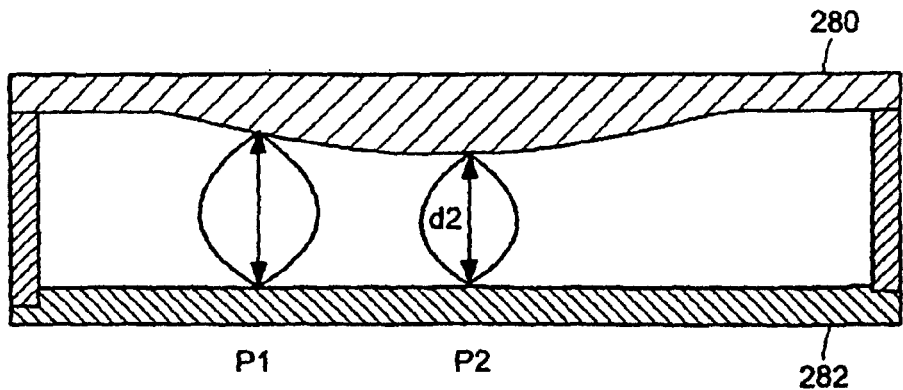
Figure 14:
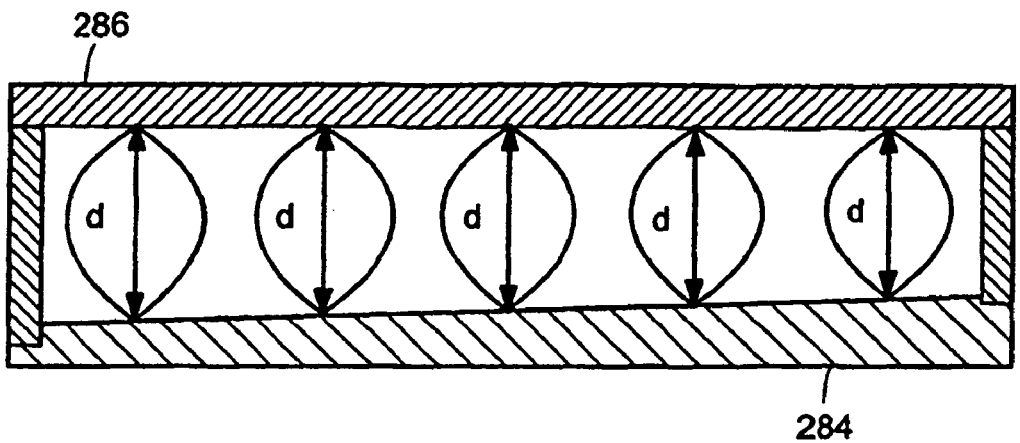
Figure 15:
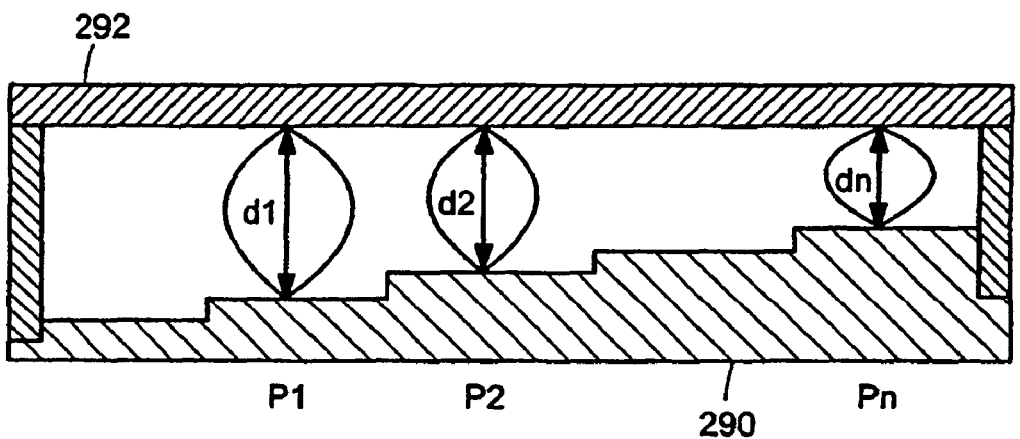

Likewise, the distance increases in the direction of flow represented by alternative arrow 276. Transducer 280 in FIG. 13 is seen to have a wave-like configuration, such that the distance between the reflector and transducer 282 decreases and then increases. It should be understood that such wave-like configuration can alternatively, or in addition, be used for the reflector associated with the transducer. FIG. 14 illustrates an alternative embodiment wherein the surface of the transducer 284 has a sloping configuration relative to reflector 286. The distance between the reflector and the transducer either increases or decreases, depending upon the direction of fluid flow through the cavity. FIG. 15 illustrates an embodiment wherein the transducer 290 has a step-wise configuration relative to reflector 292. In an embodiment corresponding to FIG. 16, transducer 294 is seen to have a wave-like configuration relative to reflector 296.

Figure 17:
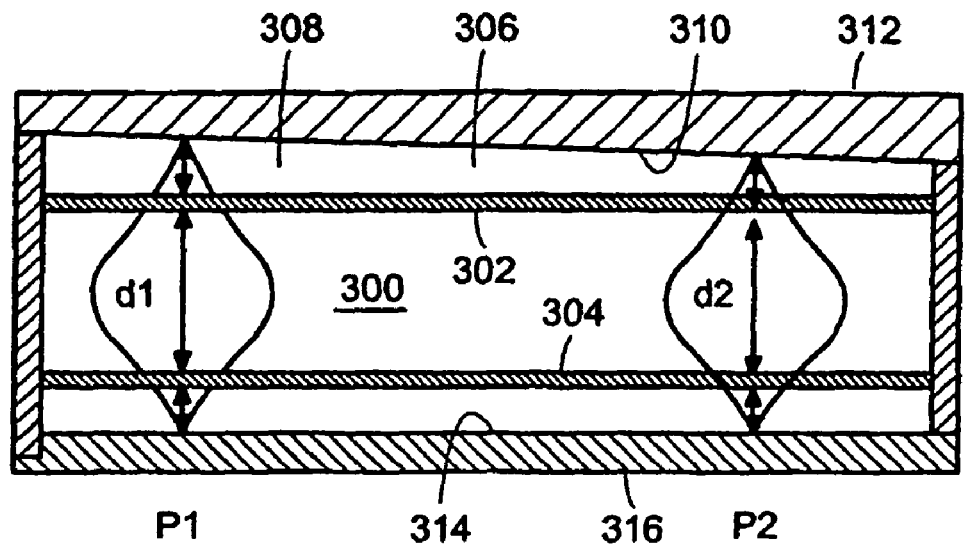
FIG. 17 is a schematic illustration of a fluid cell positioned in an ultrasonic cavity of a fluid-handling manifold in accordance with another embodiment.

In embodiments corresponding to the schematic illustration of FIG. 17, fluid-borne particles are held within a separate fluid cavity 300 formed by acoustically transparent wall members 302, 304. An acoustically conductive coupling layer 306 surrounds the fluid chamber 300 so as to fill ultrasonic cavity 308 defined by a sloping surface 310 of reflector 312 and the surface 314 of transducer 316. The fluid cartridge 300 can be fabricated either as an integral or unitary component of the fluid-handling manifold or as a sample cartridge or flow cell designed to be inserted, optionally removable inserted, into the manifold at the ultrasonic cavity. The walls 302, 304 of the flow cell preferably are transparent to ultrasound at least along the axis of standing wave field. Suitable materials are commercially available and will be recognized by those skilled in the art given the advantage of this disclosure, including the materials mentioned above. It should be recognized that the ultrasonic standing wave is established across the composite distance formed of the path links through the flow cell, the walls of the flow cell and the fluid-filled voids between the outer surface of the flow cell and the surface of the reflector or transducer as the case may be.

Figure 18:
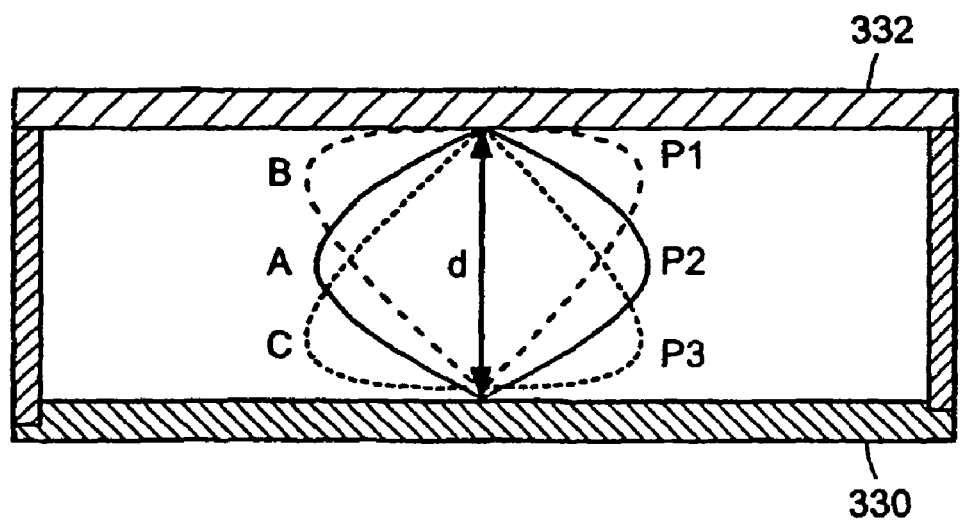
FIG. 18 is a schematic illustration of an ultrasonic cavity actuated to establish an asymmetric standing wave field in accordance with another embodiment.

FIG. 18 further illustrates the embodiments disclosed above employing an asymmetric standing wave for manipulation of fluid-borne particles. As seen in FIG. 18, a standing ultrasonic wave field in produced in an ultrasonic cavity by matching the wavelength of the ultrasonic wave with the distance "d" from the ultrasonic transducer 330 to the reflector 332. The ultrasonic field is created using transducer actuation that is substantially sinusoidal, as represented by wave line "A" in FIG. 18. As illustrated, this provides a standing wave field with pressure minima "P2" located midway between the reflector and the transducer. Upon actuation of the transducer with a signal that has a peak amplitude at a point other than 90° or 270°, the shape of the ultrasonic standing wave field changes. Specifically, the shape corresponding to line "B" or "C" can be achieved in this way, having pressure minima P1 and P3, respectively. Thus, the pressure minima in the fluid moves along the propagation axis of the standing wave field between P1 and P3. Particles collected at such pressure minima can, therefore, be moved along the propagation axis of the standing wave field by appropriately controlling the shape of the transducer actuation signal.

Figure 19:
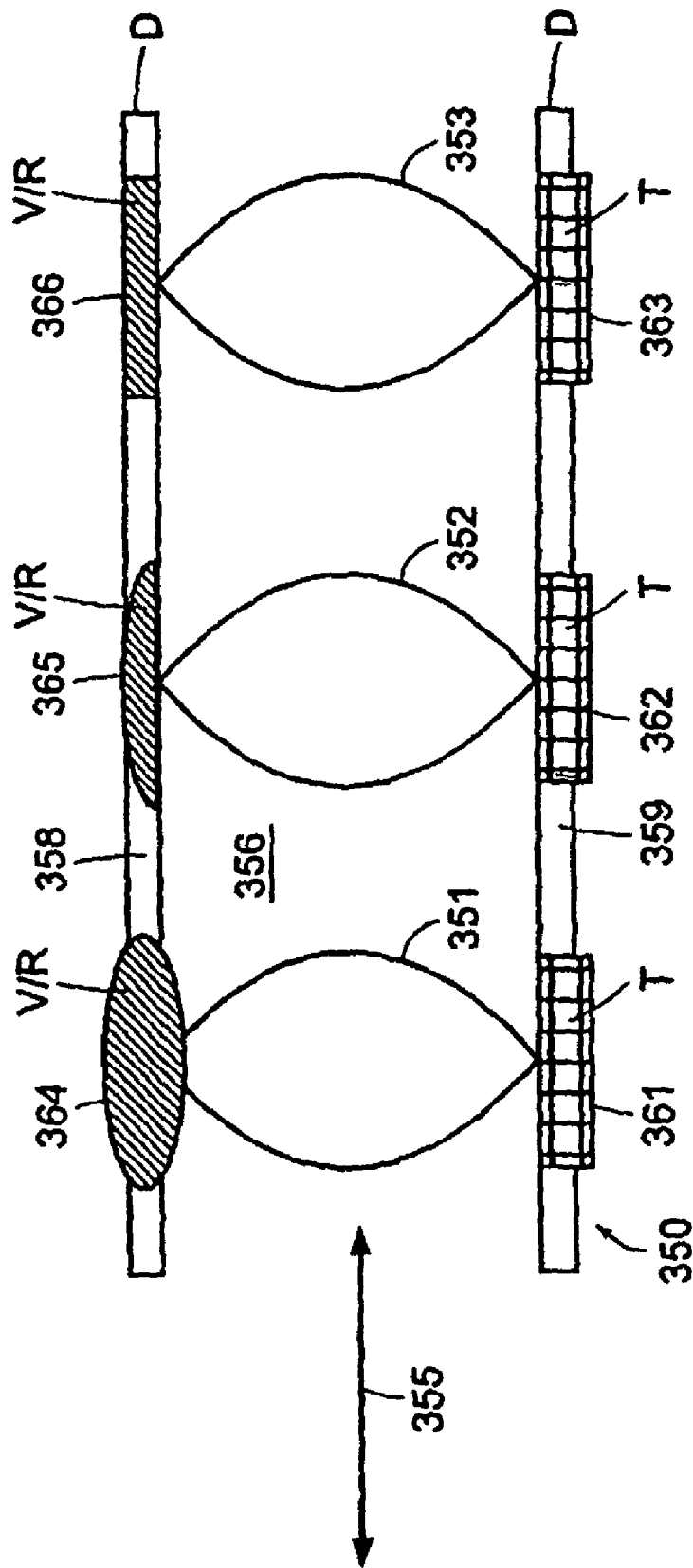
FIG. 19 is a schematic illustration of a fluid-handling device in accordance with another embodiment comprising a view-port at the ultrasonic cavity, operative for visual observation of fluid-borne particles collected and held by an ultrasonic standing wave in an ultrasonic cavity.

Referring now to FIG. 19, a fluid-handling manifold in accordance with this disclosure is seen to comprise a viewport for human or machine visual observation of fluid-borne particles ultrasonically manipulated in the manifold. In addition, the viewports are operative to admit light or other energy into the duct. Specifically, a manifold 350 is seen in the embodiment of FIG. 19 to have a set of transducers "T" labeled 361-363 in wall 359, each operative to establish a corresponding standing wave, shown by phantom lines 351-353 to collect and hold particles, e.g., solid phase extraction (SPE) particles, blood cells, etc. in a fluid flow indicated by arrow 355 in a conduit or cell 356 defined at least partly by walls 358 and 359. The dimension "D" representing the distance between the walls is preferably less than about 300 um and, more generally, is in accordance with the principles disclosed elsewhere herein. Wall 358 is seen to have three viewport reflectors 364-366 positioned opposite transducers 361-363, respectively. In accordance with certain preferred embodiments, the viewports are sufficiently clear or transparent to permit effective viewing or sensing of particles held at the corresponding standing wave in the channel 356, preferably viewing by the naked eye or with the assistance of a microscope or other device. Optionally, flow in the duct 356 is stopped during observation through the viewport. A viewport may be optically neutral or may be optically active. For example, a viewport may be configured, as in the case of viewports 364 and 365 as a lens to magnify the particles under view or to expand or limit the field of view. A lens effect or the like also may be used to focus light onto or into the particles of the standing wave. Likewise, the configuration or optical properties of the material of the viewport, being also a reflector for the standing wave, is operative to shape the ultrasonic field. Optionally, light etc. is admitted through the same viewport used for observation of the particles or through another viewport sufficiently nearby. In accordance with certain preferred embodiments, the viewports are operative to pass, optionally also to focus, light emitted by the collected particles in the duct. For example, fluorescent or luminescent emission or the like from the particles can be passed and/or focused by the viewport onto a photon capture or imaging device or other sensor or receptor positioned externally of the duct 356. Optionally such sensor or the like is directly on the exterior surface of wall 358 or is mounted at a distance above (as viewed in FIG. 19).

Figure 20:
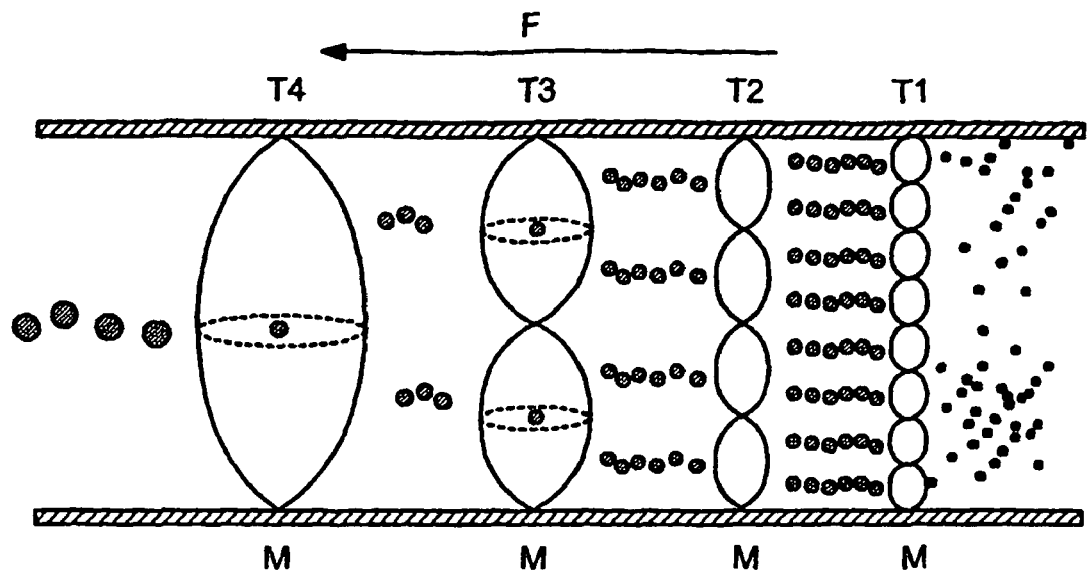
FIG. 20 is a schematic illustration of a fluid-handling device in accordance with an embodiment comprising multiple transducers that can be actuated to form separate standing wave fields that differ in frequency.

As disclosed above, certain preferred embodiments of the methods and devices disclosed here are operative to ultrasonically manipulate fluid-borne particles to cause them to agglomerate into aggregates of multiple particles. The acoustic force acting upon a given fluid-borne particle, under a given set of conditions, is a function of the actuating frequency of the acoustic force and the particle size, density and compressibility relative to the fluid in which it is carried. In accordance with certain preferred embodiments, one transducer or an arrangement of multiple transducers is used in a fluid-handling manifold to agglomerate fluid-borne particles. In embodiments employing an array of multiple transducers, they preferably are operable to produce standing wave fields of different frequencies, most preferably incrementally lower frequency in the direction of fluid flow. Higher frequency fields typically will be effective to move smaller particles to nodal positions where they will form aggregates. Thus, even if the smaller particles can not initially be readily trapped against a flowing stream, the effective size/mass of the aggregates formed by the first one or more transducers in the array typically can be more effectively manipulated, including trapping against a flowing stream, by other sound fields operated at lower frequencies by later transducer(s). In FIG. 20 transducers T1, T2, T3 and T4, each with a corresponding mirror M, operate along the same fluid duct in a fluid-handling manifold to establish a series of progressively larger (or smaller) standing wave fields. That is, the transducers are operative to form separate standing wave fields that differ from each other, preferably progressively or incrementally, in frequency. This may be caused by operating similar but separate transducers in the array at different fundamental and/or harmonic frequencies of the transducer or acoustic cavity. Transducer T1 operating at a higher frequency than transducers T2, T2 and T4 is seen to be operative to cause smaller fluid-borne particles in a fluid flowing in the direction indicated by arrow F to move to nodal positions, as they fall under the influence of transducer T1's standing wave field. The particles in some cases may be optionally trapped against flow for a period of time at the nodes established by transducer T1. After moving from the field of influence of transducer T1, the smaller particles, then collected as larger aggregates, will move to nodal positions in the field of influence of transducer T2 operating at a lower frequency. Fewer layers of aggregated particles are formed at the nodes of transducer T2, and the particles further agglomerate into yet larger aggregates. Again, as at T1, the particle aggregates optionally are trapped against flow for a period of time at the nodes established by transducer T2. After moving from the field of influence of transducer T2, the process continues in substantially the same manner at the nodes established by the transducer T3 and then at the nodes established by transducer T4. It should be understood that a larger or smaller number of transducers may be used in accordance with the principles disclosed here. At the nodal position of transducer T4, seen in FIG. 20 to be operated to form a half wavelength acoustic cavity, particles will tend to form only one or two layers which provides for simplification in subsequent processing operations.

Figure 21:
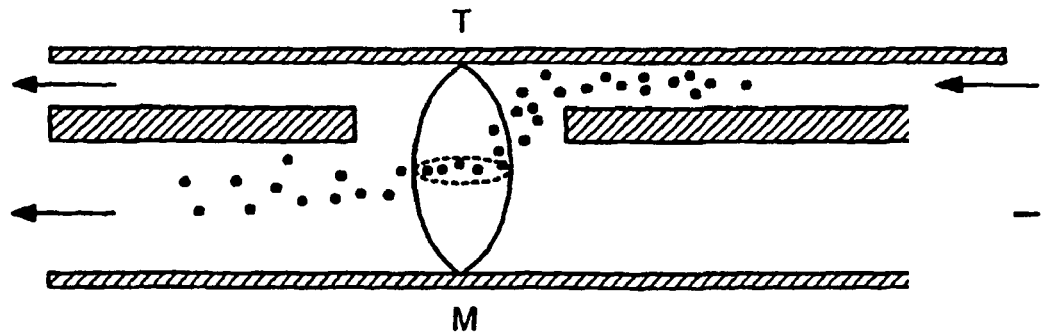
FIGS. 21 and 22 are schematic illustrations of a fluid-handling device in accordance with an embodiment wherein the node of a standing wave field is set up through an orifice communicating two adjoining fluid channels.
Figure 22:
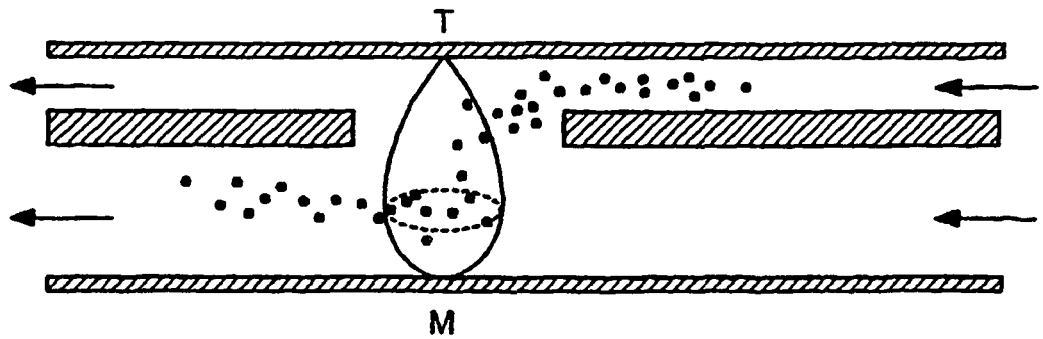

As disclosed above, certain preferred embodiments of the methods and devices disclosed here are operative to cause some or all fluid-borne particles to move from a fluid flowing in a first fluid channel of the manifold into a fluid flowing in a second fluid channel. The particles may be moved, for example through an aperture in a wall separating the two channels from each other. FIGS. 21 and 22 shows a fluid-handling manifold in two different conditions. In FIG. 21 the node of a standing wave field is set up through an orifice communicating two adjoining fluidic ducts. In FIG. 22 the node is located preferentially within the domain of one duct more than the other. For example, a 6 MHz standing wave field may set up through an orifice connecting two ducts or channels of 25 microns and 75 microns (cross-sectional diameter or diagonal dimension), respectively, and separated by a wall or layer 25 microns thick. The nodal position of the half-wavelength field is located within the 75 micron duct in FIG. 22. In FIG. 21 particles in the 25 micron duct are drawn through the orifice into the 75 micron duct. The same effect is seen in FIG. 22 wherein an asymmetric sound field establishes the nodal position preferentially within the 75 micron duct. The same effect could be achieved with channels of equal size, with an asymmetric sound field, such that the nodal position is located preferentially within one manifold more than the other. In accordance with certain alternative embodiments operative in the manner of FIGS. 21 and 22, the common volume of space at the orifice between the two channels is surrounded by spaced pillar-type structures creating a cage in which trapped particles are controllably moved back and forth, i.e., they are bi-directionally moved between the two channels by controlling the actuation of the transducer. This could be used to transfer solutes from a fluid stream in one manifold to another fluid stream in the other manifold by means of solid phase extraction.

Figure 23:
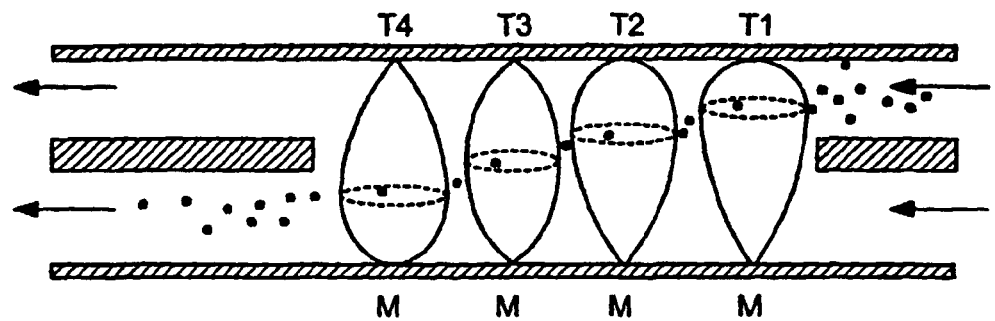
FIG. 23 is a schematic illustration of a fluid-handling device in accordance with an embodiment wherein an array of transducers is operative to establish progressively asymmetrical nodes for transferring particles from a first channel to a second channel within the manifold.

FIG. 23 illustrates certain preferred embodiments wherein particle movement between tiered channels, that is, channels or ducts overlying each other in the manifold, is achieved by the use of an array of asymmetric standing wave fields. An array of transducers T1-T4 forms a corresponding set of adjacent, but otherwise substantially independent standing waves, each of which differs in its asymmetry from adjacent nodes, typically differing incrementally or otherwise progressively. Collectively, the set of standing waves form a discontinuous train of standing waves in which the individual stationary nodal positions are incrementally advanced one to the next, from the level or zone of one channel to the level or zone of the other channel. The progressively positioned nodes are operative to progressively move fluid-borne particles in the first stream to the nodal positions of the different standing wave fields, and by doing so, to progressively move them from the first flow stream to the adjacent contacting flow stream. It should be understood that alternative embodiments are operative to move fluid-borne particles in this manner from a first fluid stream to a second stream flowing countercurrent to the first stream.

Figure 24:
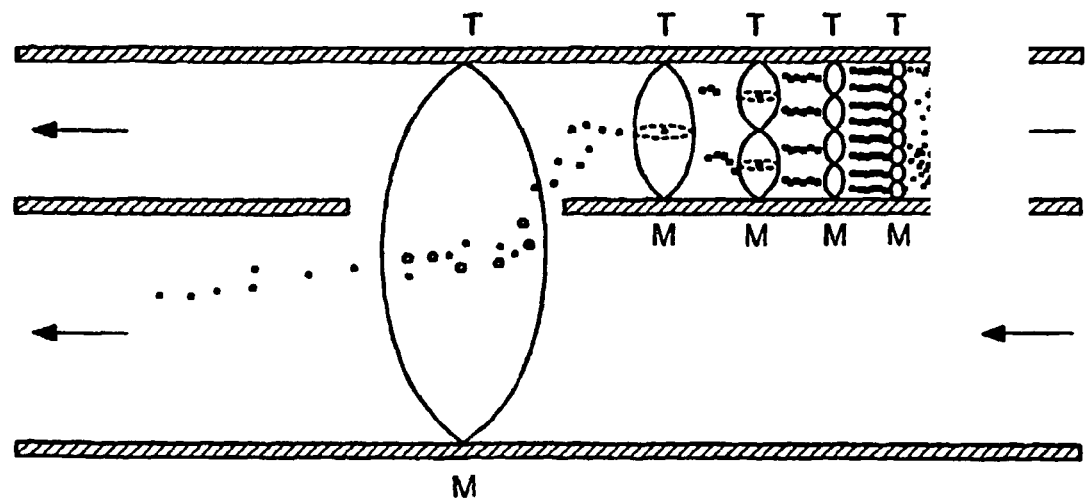
FIG. 24 is a schematic illustration of a fluid-handling device in accordance with an embodiment wherein an array of transducers is operative to establish progressively sized nodes.

FIG. 24 illustrates another preferred embodiment wherein an array of transducers in a first channel is operative to agglomerate fluid-borne particles into larger aggregates, and an additional transducer is operative to establish a standing wave field at an aperture between the first channel and a second channel to move the aggregates into the second channel. Thus, small particles are condensed into larger particles and then transferred from one fluid duct to another by means of a standing wave field set up within an orifice between those two adjacent flow streams. In an exemplary embodiment in accordance with FIG. 24, a 12 MHz standing wave field with a 125 micron separation between transducer and reflector will produce one or more nodal positions and be more effective at moving the position of relatively small particles within the sound field than a similar sound field in the same manifold but operated at a lower frequency, e.g. 6 MHz. If the aggregated particles then proceed to another sound field which is operated at a lower frequency, such as a 6 MHz field, it is more likely that they can be effected (e.g., trapped or moved against flow) by the sound field than if they had not been first aggregated by passage through a higher frequency sound field. In such exemplary embodiment, the aggregated particles move from the 12 MHz to the 6 MHz field. Similarly, the 12 MHz field is preceded by an even higher frequency sound field which affects the position of even smaller particles and therefore is effective to agglomerate them. A 2 MHz sound field is incorporated with the associated reflector located within (e.g., below) a second duct lying beneath the first duct. Depending upon the flow velocity conditions and strength of the sound field, particles will move to the nodal position of the 2 MHz half wavelength field is seen to be positioned substantially within the lower duct. Thus, fluid-borne particles are agglomerated in a series of transducer stations and then moved into an adjacent channel by operation of an additional transducer station.

Figure 25:
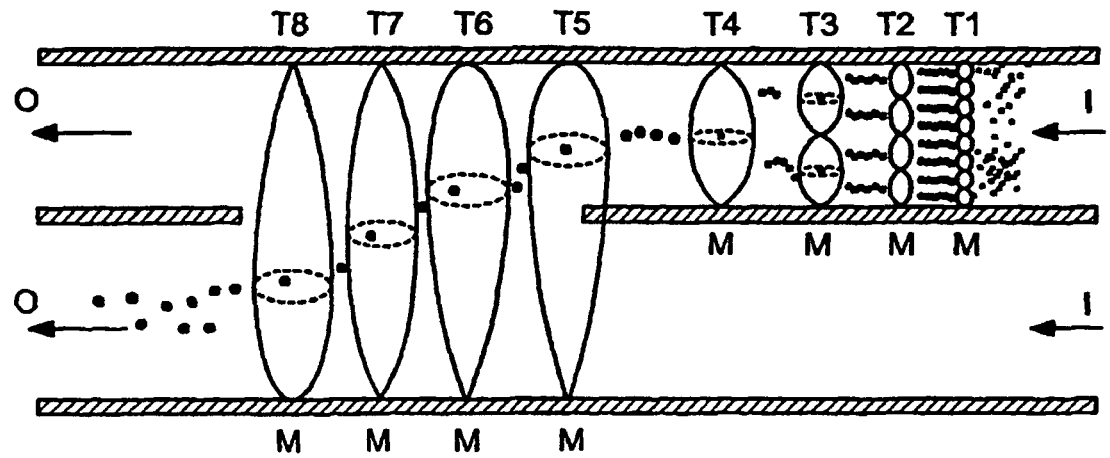
FIG. 25 is a schematic illustration of a fluid-handling device in accordance with an embodiment wherein an array of transducers is operative to establish progressively sized nodes and to establish progressively asymmetrical nodes for transferring particles from a first channel to a second channel within the manifold.

FIG. 25 illustrates another preferred embodiment wherein an array of transducers T1-T4 in a first channel is operative to agglomerate fluid-borne particles into larger aggregates, and an additional array of transducers T5-T8 is operative to establish a series of progressively, incrementally asymmetric standing wave fields at an aperture between the first channel and a second channel to move the aggregates into the second channel. Thus, small particles are condensed into larger particles and then transferred step-wise from one fluid duct to another by means of the second array of transducers.

Figure 26:
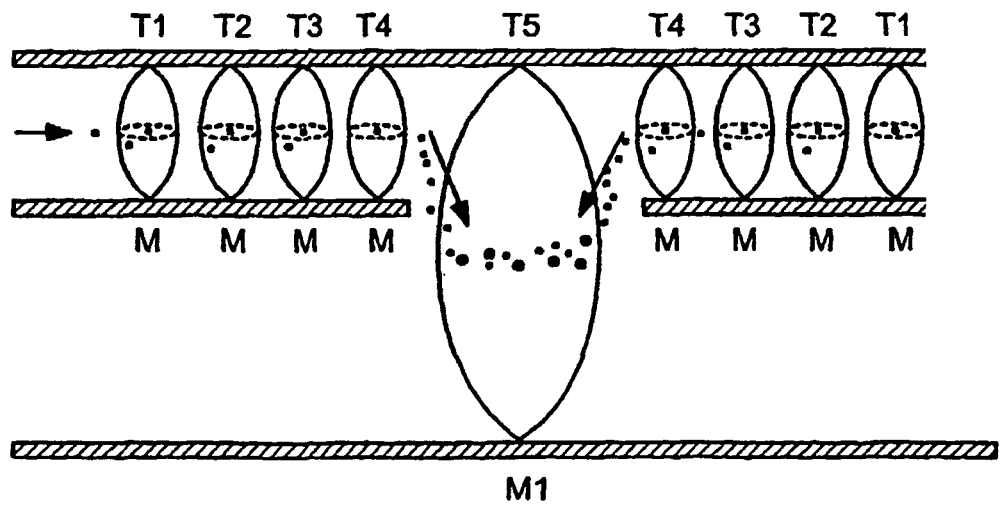
FIG. 26 is a schematic illustration of a fluid-handling device in accordance with another embodiment, wherein a series of concentric ring transducers with mirrors are operative to be programmably actuated to control progressive centripetal movement of fluid-borne particles.

FIG. 26 illustrates another preferred embodiment wherein an array of concentric ring transducers T1-T4 in a first channel in a fluid-handling manifold is operative to establish a corresponding series of concentric ring standing wave fields to cause centripetal movement of particles and through-layer particle transport. More specifically, fluid-borne particles, i.e., in this case suspended solid particulate material in the fluid flowing in a first channel, the top channel as viewed in FIG. 26, are transferred to another channel through an aperture that provides fluid communication between the two channels. FIG. 26 shows that the series of concentric ring transducers, including center transducer T5, each has a corresponding mirror M and can be controlled, preferably being programmably actuated, to cause progressive centripetal movement of particles towards the center. The central transducer T5 is aligned with optional mirror M1 incorporated within or on the bottom wall of the lower channel.

Transducer T5 propagates sound through the aperture, a hole in the dividing wall between the two channels, to be reflected or the like by mirror M1. The nodal position of this acoustic field, preferably a half-wavelength, centrally-located field, is within the domain of the lower channel. Particles are thus transported from one channel to another. The fluid in the upper and lower adjoining ducts may be similar in composition or different, e.g. miscible or immiscible with each other.

Figure 27:
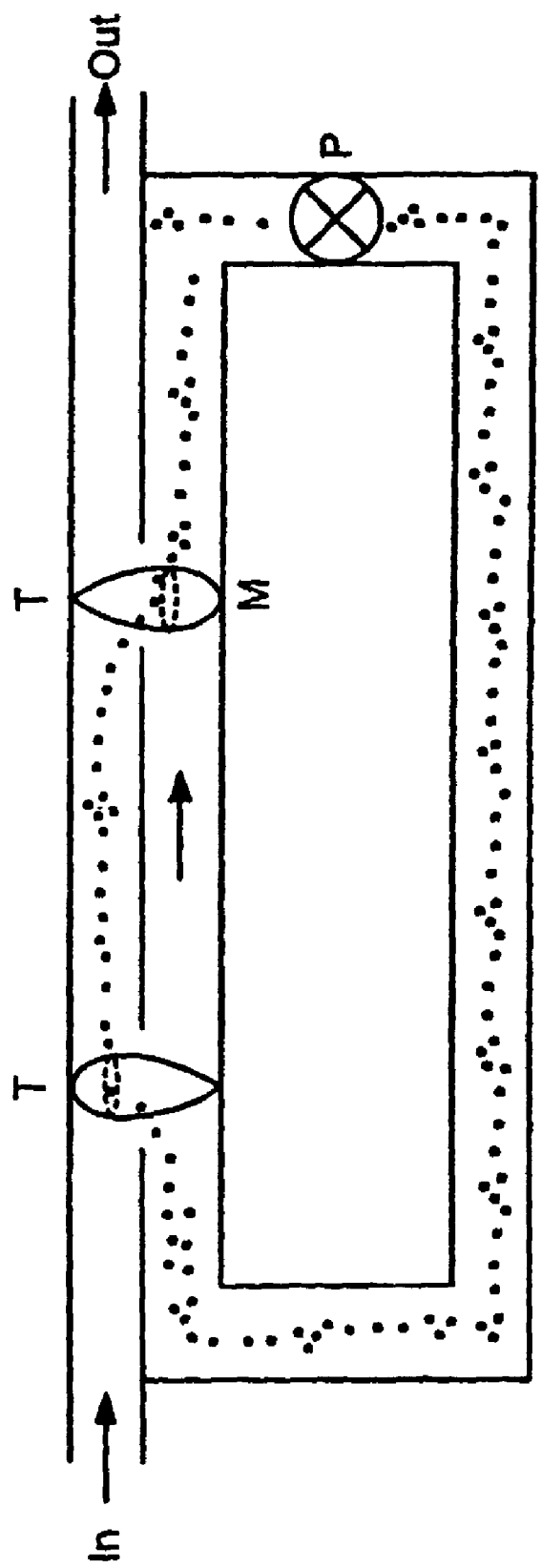
FIG. 27 is a schematic illustration of a fluid-handling device in accordance with an embodiment wherein an array of transducers is operative to establish asymmetrical nodes for transferring particles from a flow stream in a manifold into another stream in an adjacent channel across a microcontactor interface.

FIG. 27 illustrates another preferred embodiment, operative as an ultrasonically enhanced, continuous-flow, cross-stream chemical extractor. FIG. 27 illustrates manipulation of fluid-borne particles from one flow stream into another across a microcontactor interface employing asymmetric standing nodes or other transducer arrangements as described above. The fluid-borne particles, e.g., SPE beads, catalysts, etc., are first moved into a loop flow channel comprising the extractor, by moving toward the node position of the first-encountered asymmetric sound field established by a transducer T an associated mirror M. The particles then are moved back again to the original flow stream, if desired, e.g., for possible re-use in a semi-closed loop set-up. Pumping mechanism (P) is operative to transport the fluid and contained particles within the closed loop circuit around in a cyclical manner. Optionally a counter-flow mode is employed. With this arrangement, one or more component chemical species in one flow stream are transferred to another flow stream in which, due to the closed-loop arrangement, it becomes progressively more concentrated.

Figure 28:
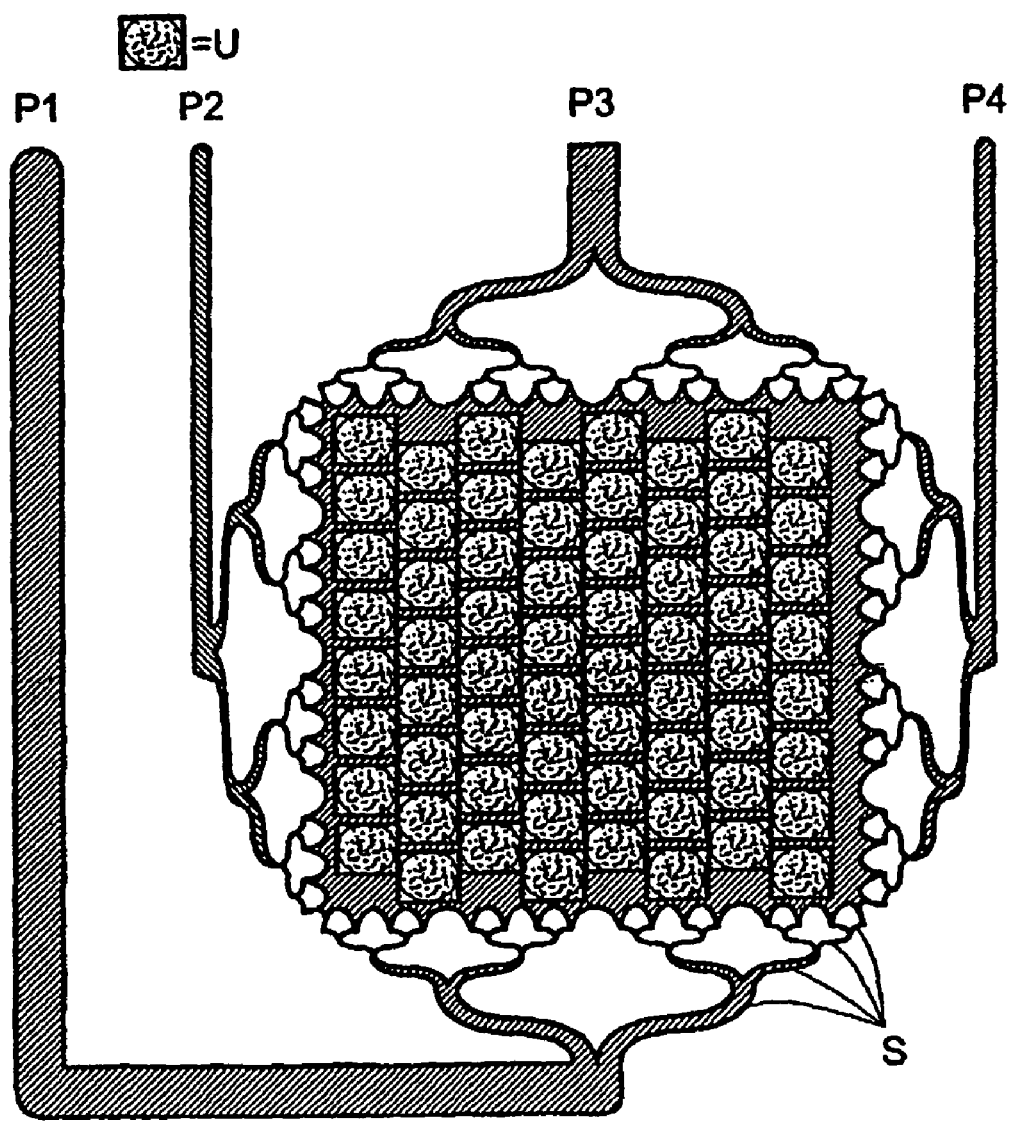
FIG. 28 is a schematic illustration of a fluid-handling device in accordance with an embodiment comprising multiple transducers arranged in staggered geometrical matrix layout.
Figure 29:
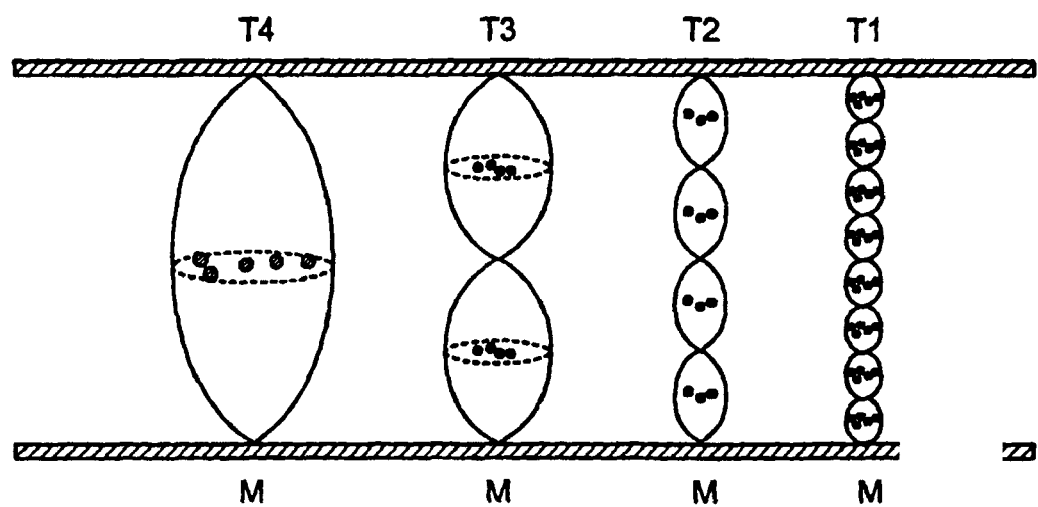
FIG. 29 is a schematic illustration of a fluid-handling device in accordance with the embodiment of FIG. 28 showing the standing waves established by each of the arrayed transducers having a different number of nodes dependent upon the actuation frequency of the transducer in relation to the distance between transducer and mirror across the ultrasonic cavity in the manifold.

The preferred embodiment schematically illustrated in FIG. 28 incorporates multiple transducers arranged in staggered geometrical matrix layout. In this design 64 transducers each 3 mm in diameter are arranged in 8 rows of 8 elements each, spanning an ultrasonic cavity of internal dimensions: 42 mm (width) by 42 mm (length) by various depths ranging from 1 um to 300 um according to the desired rate of throughput and velocity of liquid flow. The ultrasonic cavity, connecting ducts and other associated components may be incorporated within a manifold configured, for example, of a planar card-like cartridge measuring 54 mm in width by 85.6 mm in length and 10.5 mm in height. The transducers are provided with mirrors, also referred to as reflectors, for the establishment of standing wave sound fields (denoted "U" in FIG. 28). Each standing wave may be established to produce one or more nodes dependent upon the actuation frequency of the transducer in relation to the distance between transducer and mirror, as shown in FIG. 29. In FIG. 28 fluid ports P1-P4 provide access for liquid matrices to be transported through the ultrasonic chamber. Liquid matrices may be introduced which contain, for example, solid phase extraction media (such as silica particles, polymer particles, resins, molecularly imprinted polymers, etc.). Solid phase extraction media may be trapped at the node(s) of standing wave fields and held against the flow of fluid. Quantities of material trapped will vary, depending largely on flow velocity, particle size, porosity and density, and frequency of the actuating sound field. For example, a single 7.5 MHz standing wave field produced by a 3 mm diameter transducer in an ultrasonic cavity of 100 micron path length with a flow stream of 50 uL/min will hold approximately 20 mg of 3 micron diameter solid phase extraction media (silica), against the flow of the fluid. The flow of fluid entering the ultrasonic cavity may be distributed evenly or otherwise across two or more fluidic openings into the cavity by the use of flow distributor S in FIG. 28. This allows the fluid to be introduced so that any variations in the nature of the fluid passing through inlet/outlet ports of the manifold is mirrored evenly across the multi-site levitated bed of solid phase extraction media. In one specific design that has an ultrasonic cavity depth (path length) of 250 microns and width/depth of 42 mm, with standing wave fields providing 4 nodal positions each, fluid may be transported through the ultrasonic cavity at rates of 1 mL/min using actuation voltages of 15 volts and may be considerably increased where higher power actuation signals are provided. Fluids may be programmably transported through the ultrasonic cavity so that one or more species of chemical constituent are absorbed onto the trapped particles from a sample fluid and subsequently eluted from those particles by the transportation of a different fluid through the ultrasonic cavity. Optical, electrical and or magnetic excitation of the solid phase extraction media may be used to assist the adsorption and desorption events.

As noted above, the fluid-handling manifolds disclosed here may take any of numerous forms, e.g., a cartridge or a component of a cartridge for performing one or more operations on a fluid, for example, fluid analysis, testing, detection or the like, such as by liquid chromatography, electrophoresis, or other liquid separation and analytical techniques. Any of various different operations may be performed by the fluid-handling manifold in addition to ultrasonic manipulation of fluid-borne particles, employing, for example, heating, cooling, electrical or electromagnetic or acoustical (e.g., ultrasonic) forces, pressure differentials, etc. Exemplary unit operations which may be performed by various different embodiments of the fluid-handling manifold disclosed here include fluid mixing, reacting, analyzing, extraction, amplification or focusing or concentration, labeling, filtering, selection, purification, etc. Information such as the identity of the fluid-handling manifold, the results of any such operation(s) and/or when they occurred or the conditions at that time may optionally be digitally or otherwise recorded, such as in an on-board memory chip or the like carried by the fluid-handling manifold or by another component of a system in which the fluid-handling manifold is employed. One or more of the aforesaid operations may be integrated into the fluid manifold.

The fluid-handling manifolds disclosed here preferably are "microfluidic" in that they operate effectively on micro-scale fluid samples, typically having fluid flow rates as low as about 1 ml/min, preferably 100:1 min or less, more preferably 10:1/min or less, most preferably about 1:1/min or less, for example 100 nanoliters/min. Total fluid volume for an LC or other such fluid separation performed by fluid-handling manifolds disclosed here, e.g., in support of a water quality test to determine the concentration of an analyte in the water being tested, in accordance with certain preferred embodiments, can be as small as about 10 ml or less, or 1 ml or less, preferably 100 microliters or less, more preferably 10 microliters or even 1 microliter or less, for example, about 100 nanoliters. As used herein, the term "microscale" also refers to flow passages or channels and other structural elements of the fluid-handling manifolds. For example, microchannels of the fluid-handling manifold preferably have a cross-sectional dimension (diameter, width or height) between 500 microns and 100 nanometers. Thus, at the small end of that range, the microchannel has cross-sectional area of about 0.01 square microns. Such microchannels within the fluid-handling manifold, and chambers and other structures within the fluid-handling manifold, when viewed in cross-section, may be triangular, ellipsoidal, square, rectangular, circular or any other shape, with at least one and preferably all of the cross-sectional dimensions transverse to the path of fluid flow is microscale. It should be recognized, that one or more layers of the fluid-handling manifold may in certain embodiments have operative features, such as fluid channels, reaction chambers or zones, accumulation sites etc. that are larger than microscale. The fluid-handling manifolds disclosed here provide effective fluid analysis systems with good speed of analysis, decreased sample and solvent consumption, the possibility of increased detection efficiency, and in certain embodiments disposable fluid-handling devices.

Microfluidic embodiments of the fluid-handling manifolds disclosed here provide significant commercial advantage. Less sample fluid is required, which in certain applications can present significant cost reductions, both in reducing product usage (for example, if the test sample is taken from a product stream) and in reducing the waste stream disposal volume. In addition, the microfluidic features of such fluid-handling manifolds can, in accordance with preferred embodiments, be produced employing MEMS and other known techniques suitable for cost effective manufacture of miniature high precision devices. The micro-scale fluid flow channel(s) and other operational features and components of the microfluidic fluid-handling manifold, such as components for liquid chromatography or other fluid separation method, heating or cooling fluid handled by the assembly, generating electrical or electromagnetic or acoustical (e.g., ultrasonic) forces on the fluid, generating high pressures or pressure differentials, fluid mixing, reacting, analyzing, extraction, amplification or focusing or concentration, labeling, filtering, selection, purification, etc. can be integrated into the fluid-handling manifolds, mounted onto the fluid-handling manifold as an on-board component or incorporated elsewhere in the fluid-handling manifold. Such operational devices, including devices integrated as an external component-on-board mounted in fluid-tight fashion to the surface of the fluid-handling manifold and/or devices embedded within the body of the fluid-handling manifold, in accordance with preferred embodiments are micro-scale devices, as defined above.

Exemplary of the components-on-board suitable for integration with the fluid-handling manifolds disclosed here are heaters, coolers (e.g., electrical heating elements and/or refrigeration elements), pumps, fluid reservoirs, etc. Necessary or desired functions not performed by a suitable component-on-board can be performed by other equipment associated with the fluid-handling manifold. An electrical element may be integrated into the fluid-handling manifold, with electrical contacts for power mated to matching electrical contacts in a larger associated device which receives the fluid-handling manifold. Alternatively, the larger associated device may include internal or external heating means, such as a laser or other source of electromagnetic energy. A microprocessor may be used to regulate fluid flow, heating and/or other functions of the fluid-handling manifold. A thermocouple, thermistor or temperature-sensitive diode may be provided in the fluid-handling manifold in electrical contact with the associated device to allow such microprocessor or other electronic controller to detect and maintain desired temperatures. A cooling element, such as a miniature thermoelectric heat pump (Materials Electronic Products Corp., Trenton, N.J.), may be used.

In accordance with preferred embodiments, microscale fluid flow channels within generally planar fluid-handling manifold are formed at surface-to-surface interfaces between laminated layers of the fluid-handling manifold. Multiple levels of microchannels can be formed, for example, by a PEEK or other plastic plate or disk having micromachined grooves on both an upper and lower surface, sandwiched between other layers of the fluid-handling manifold. A through-hole micromachined or otherwise formed in the plastic plate passing from an upper surface groove to a lower surface groove provides a fluid communication via. In certain preferred embodiments one or both of the sandwiching layers of the fluid-handling manifold is a flexible sheet or film. As used here, the term "generally planar fluid-handling manifolds" means card or cartridge-like manifolds, optionally being curvo-planar or otherwise irregular, but typically being rectilinear or right-cylindrical, and having a thickness less than about one third, preferably less than one quarter, more preferably less than about one fifth, e.g., about one sixth or less, the largest dimension of the major (i.e., largest) surface of the laminated fluid-handling manifold (measured without including any external components mounted on-board the fluid-handling manifold or electrical leads or conduits carrying sample fluid to or from the manifold). One or both of the sandwiching layers can be welded or otherwise bonded, selectively or not, to the micromachined layer to provide fluid-tight sealing along the microchannels. Additional levels of microchannels are provided by stacking additional micromachined plates in the fluid-handling manifold. Directional references used here are for convenience only and not intended to limit the orientation in which the fluid-handling manifolds are used. In general, the fluid-handling manifolds can be used in any orientation; solely for purposes of discussion here, they are assumed to be in the orientation shown in the drawings appended hereto. Those skilled in the art will recognize, given the benefit of this disclosure, that vias and other channels of the fluid-handling manifolds can have any suitable configuration, including straight, curvo-linear, serpentine or spiral. Their cross-sectional configuration can be regular, i.e., uniform, or irregular, to suit the needs of an intended application.

In certain preferred embodiments, fluid-handling manifolds have laminated layers, wherein at least one layer is formed of plastic and the fluid-handling manifold is operative and fluid tight at high fluid pressure, e.g., at fluid pressures in excess of 100 psig, preferably in excess of 200 psig, more preferably in excess of 300 psig, most preferably at pressures greater than 500 psig. Especially preferred embodiments are operative, including being fluid-tight along the periphery of channels within the fluid-handling manifold, even at fluid pressure in excess of 1000 psig. High pressure embodiments employing plastic fluid-handling manifold layers provide significant advantages in manufacturing cost and flexibility. In accordance with certain such preferred embodiments, rigid plates sandwich plastic layers between them. The plastic layers optionally are welded one to another and the rigid plates sandwiching the multiple plastic layer between them are formed of metal and are fastened directly to each other. As used here, direct fastening means that a bolt or other fastener has compressive contact with the rigid sandwiching plates. Preferably multiple bolts or the like extend from one to the other of the rigid sandwiching plates. In accordance with certain preferred embodiments, grooves for fluid flow channels can be micromachined, laser cut or otherwise milled or formed in the inside surface of one or both metal (or other rigid material) clamping plates that may be, e.g., 3/16 to 3 inch thick. When the fluid-handling manifold is assembled, a layer of PEEK or other plastic, e.g., 0.003-0.005 inch thick clamped between the plates, in cooperation with the clamping plates grooves, defines fluid channels of the resulting fluid-handling manifolds. Through holes in the PEEK layer can serve as vertical vias in the fluid-handling manifold to provide fluid communication from channels in the inside surface of the top clamping plate to those in the lower clamping plate.

In accordance with certain preferred embodiments, the fluid-handling manifolds has at least one electronic memory component operatively connected to another component of the manifold operative to generate an electronic signal corresponding to a detected or measured fluid component or condition or characteristic. The memory component is connected to the operative component to receive and record the electronic signal. In preferred embodiments, the fluid-handling device further comprises electronic communication means for communication with the memory component. Suitable I/O devices for uploading signals to the memory component or downloading information stored on it to a central computer or telecommunication device or the like will be apparent to those skilled in the art given the benefit of this disclosure, and include, for example, PCMCIA-type, Universal Serial Bus and IEEE 1394 (FireWire, i.Link) electronic communication ports or on-board transceivers for example Bluetooth™ short range radio. As stated above, preferred embodiments of the fluid handling devices disclosed here are operative to perform, or are adapted to function in a larger system which performs, any of various different liquid separation test or analysis methods. Liquid separation method parameters can be stored in a memory component of the device or in a memory component of the larger system and, in accordance with preferred embodiments; such information stored in the memory component defines a liquid separation. From the above disclosure and detailed description of various preferred embodiments, it will be recognized by those skilled in the art, that good functionality is provided by the novel devices and methods disclosed here, including uses in fluid-handling applications such as liquid chromatography separations and analyses, biological fluid separations and analysis, etc. The invention has been shown and described with reference to certain exemplary embodiments. It will be apparent to those skilled in the art, however, that various changes and additions can be made in the form and details of the devices and methods disclosed here without departing from the true spirit and scope of the invention as defined by the following claims.

What is claimed is:

1. A fluid-handling device for ultrasonic manipulation of fluid-borne particles, comprising, in combination:
   a fluid-handling manifold having a fluid inlet port and defining a fluid-handling void comprising at least a first fluid channel;
   a second fluid channel in fluid communication with the first fluid channel at an intersection within the ultrasonic cavity; and
   an ultrasonic particle manipulator defining an ultrasonic cavity and comprising at least one ultrasonic transducer, the first fluid channel extending from the inlet port to the ultrasonic cavity and the ultrasonic particle manipulator being operative to establish an ultrasonic standing wave field in particle-bearing fluid in the first fluid channel at the ultrasonic cavity,
   wherein the ultrasonic cavity has a non-uniform configuration;
   wherein the first fluid channel and the second fluid channel extend substantially parallel each other on opposite sides of a dividing wall between them, and
   wherein the intersection comprises a passageway through the dividing wall.

2. The fluid-handling device of claim 1 for ultrasonic manipulation of fluid-borne particles, wherein the ultrasonic cavity has a configuration that is non-uniform in the direction of flow.

3. The fluid-handling device of claim 1 for ultrasonic manipulation of fluid-borne particles, wherein the ultrasonic cavity has a cross-sectional configuration that is non-uniform in a direction substantially transverse to the direction of flow in the first fluid channel.

4. The fluid-handling device of claim 1 for ultrasonic manipulation of fluid-borne particles, wherein the dividing wall between the first and second fluid channels is 10 microns to 30 microns thick.

5. A fluid-handling device for ultrasonic manipulation of fluid-borne particles, comprising, in combination:
   a fluid-handling manifold having a fluid inlet port and defining a fluid-handling void comprising at least a first fluid channel; and
   an ultrasonic particle manipulator defining an ultrasonic cavity and comprising at least one ultrasonic transducer, the first fluid channel extending from the inlet port to the ultrasonic cavity and the ultrasonic particle manipulator being operative to establish an ultrasonic standing wave field in particle-bearing fluid in the first fluid channel at the ultrasonic cavity,
   wherein the fluid-handling void further comprises a second fluid channel in fluid communication with the first fluid channel at an intersection within the ultrasonic cavity;
   the ultrasonic particle manipulator is operative to establish an ultrasonic standing wave field having an axial direction of standing wave propagation substantially perpendicular to the direction of fluid communication through the intersection;
   the cross-sectional configuration of the ultrasonic cavity is non-uniform in the direction of fluid communication through the intersection; and
   the ultrasonic particle manipulator is operative to collect fluid-borne particles from fluid in the first fluid channel and move collected fluid-borne particles through the intersection to the second fluid channel by varying the actuation frequency of the ultrasonic transducer.

6. The fluid-handling device of claim 5 for ultrasonic manipulation of fluid-borne particles, wherein the ultrasonic particle manipulator is operative to selectively position an ultrasonic standing wave field in the second fluid channel.

7. The fluid-handling device of claim 5 for ultrasonic manipulation of fluid-borne particles, wherein the ultrasonic particle manipulator is operative to selectively position an ultrasonic standing wave field in the intersection of the first and second fluid channels.

8. The fluid-handling device of claim 5 for ultrasonic manipulation of fluid-borne particles, wherein the dimension of the ultrasonic cavity in the axial direction of standing wave propagation increases stepwise along the direction of fluid communication through the intersection.

9. The fluid-handling device of claim 5 for ultrasonic manipulation of fluid-borne particles, wherein the dimension of the ultrasonic cavity in the axial direction of standing wave propagation increases continuously along the direction of fluid communication through the intersection.

10. The fluid-handling device of claim 5 for ultrasonic manipulation of fluid-borne particles, wherein the dimension of the ultrasonic cavity in the axial direction of standing wave propagation varies wave-like along the direction of fluid communication through the intersection.

11. The fluid-handling device of claim 5 for ultrasonic manipulation of fluid-borne particles, wherein a surface of the ultrasonic cavity is formed by the ultrasonic transducer and has a stepwise configuration along the direction of fluid communication through the intersection.

12. The fluid-handling device of claim 5 for ultrasonic manipulation of fluid-borne particles, wherein a surface of the ultrasonic cavity is formed by the ultrasonic transducer and has a sloping configuration along the direction of fluid communication through the intersection.

13. The fluid-handling device of claim 5 for ultrasonic manipulation of fluid-borne particles, wherein a surface of the ultrasonic cavity is formed by the ultrasonic transducer and has a wave-like configuration along the direction of fluid communication through the intersection.

14. The fluid-handling device of claim 5 for ultrasonic manipulation of fluid-borne particles, wherein a surface of the ultrasonic cavity is formed by an ultrasonic reflector and has a stepwise configuration along the direction of fluid communication through the intersection.

15. The fluid-handling device of claim 5 for ultrasonic manipulation of fluid-borne particles, wherein a surface of the ultrasonic cavity is formed by an ultrasonic reflector and has a sloping configuration along the direction of fluid communication through the intersection.

16. The fluid-handling device of claim 5 for ultrasonic manipulation of fluid-borne particles, wherein a surface of the ultrasonic cavity is formed by the ultrasonic reflector and has a wave-like configuration along the direction of fluid communication through the intersection.

17. The fluid-handling device of claim 5 for ultrasonic manipulation of fluid-borne particles, wherein the first fluid channel and the second fluid channel intersect each other substantially tangentially.

18. The fluid-handling device of claim 5 for ultrasonic manipulation of fluid-borne particles, wherein the intersection between the first fluid channel and the second fluid channel comprises an orifice.

19. A fluid-handling device for ultrasonic manipulation of fluid-borne particles, comprising, in combination:
    a fluid-handling manifold having a fluid inlet port;
    a first fluid channel in fluid communication with the fluid inlet port;
    an ultrasonic particle manipulator comprising at least one ultrasonic transducer and an acoustic reflector positioned opposite the ultrasonic transducer, the ultrasonic transducer and the acoustic reflector cooperatively defining between them an ultrasonic cavity and operative to separate fluid-borne particles from fluid flowed through the ultrasonic cavity by establishing an ultrasonic standing wave field in a portion of the first fluid channel extending through the ultrasonic cavity; and
    a second fluid channel in fluid communication with the first fluid channel at an intersection within the ultrasonic cavity,
    wherein the first fluid channel and the second fluid channel extend substantially parallel each other on opposite sides of a dividing wall between them, and
    wherein the intersection comprises a passageway through the dividing wall.

20. The fluid-handling device of claim 19 for ultrasonic manipulation of fluid-borne particles, wherein the spacing between the ultrasonic transducer and the acoustic reflector is not more than 300 microns.

21. The fluid-handling device of claim 19 for ultrasonic manipulation of fluid-borne particles, wherein the ultrasonic particle manipulator is operative to establish an ultrasonic standing wave field having an axial direction of standing wave propagation substantially perpendicular to the direction of fluid communication through the intersection.

22. The fluid-handling device of claim 19 for ultrasonic manipulation of fluid-borne particles, wherein the cross-sectional configuration of the ultrasonic cavity is non-uniform in the direction of fluid communication through the intersection.

23. The fluid-handling device of claim 19 for ultrasonic manipulation of fluid-borne particles, wherein the ultrasonic particle manipulator is operative to collect fluid-borne particles from fluid in the first fluid channel and move collected fluid-borne particles through the intersection to the second fluid channel by varying the actuation frequency of the ultrasonic transducer.

24. A fluid-handling device for ultrasonic manipulation of fluid-borne particles, comprising:
    an ultrasonic particle manipulator defining an ultrasonic cavity and comprising at least one ultrasonic transducer and an acoustic reflector;
    a first fluid channel extending into the ultrasonic cavity; and
    a second fluid channel in fluid communication with the first fluid channel at an intersection within the ultrasonic cavity,
    wherein the first fluid channel and the second fluid channel extend substantially parallel each other on opposite sides of a dividing wall between them, and the intersection comprises a passageway through the dividing wall,
    wherein the ultrasonic particle manipulator is operative to establish an ultrasonic standing wave field in fluid in the ultrasonic cavity, and
    wherein the spacing between the ultrasonic transducer and the acoustic reflector is not more than 300 microns.

25. The fluid-handling device of claim 24 for ultrasonic manipulation of fluid-borne particles, wherein the ultrasonic cavity has a non-uniform configuration.

26. The fluid-handling device of claim 24 for ultrasonic manipulation of fluid-borne particles, wherein the ultrasonic particle manipulator is operative to establish an ultrasonic standing wave field having an axial direction of standing wave propagation substantially perpendicular to the direction of fluid communication through the intersection.

27. The fluid-handling device of claim 24 for ultrasonic manipulation of fluid-borne particles, wherein the cross-sectional configuration of the ultrasonic cavity is non-uniform in the direction of fluid communication through the intersection.

28. The fluid-handling device of claim 24 for ultrasonic manipulation of fluid-borne particles, wherein the ultrasonic particle manipulator is operative to collect fluid-borne particles from fluid in the first fluid channel and move collected fluid-borne particles through the intersection to the second fluid channel by varying the actuation frequency of the ultrasonic transducer.

29. The fluid-handling device of claim 24 for ultrasonic manipulation of fluid-borne particles, wherein the dimension of the ultrasonic cavity in the axial direction of standing wave propagation increases stepwise along the direction of fluid communication through the intersection.

* * * * *